(12) United States Patent
de la Monte et al.

(10) Patent No.: US 9,717,719 B2
(45) Date of Patent: Aug. 1, 2017

(54) TREATMENT, PREVENTION, AND REVERSAL OF ALCOHOL-INDUCED LIVER DISEASE

(75) Inventors: Suzanne Marie de la Monte, East Greenwich, RI (US); Jack Raymond Wands, East Greenwich, RI (US)

(73) Assignee: Rhode Island Hospital, Providence, RI (US)

( * ) Notice: Subject to any disclaimer, the term of this patent is extended or adjusted under 35 U.S.C. 154(b) by 846 days.

(21) Appl. No.: 12/310,832

(22) PCT Filed: Sep. 10, 2007

(86) PCT No.: PCT/US2007/019610
§ 371 (c)(1),
(2), (4) Date: Oct. 7, 2009

(87) PCT Pub. No.: WO2008/030595
PCT Pub. Date: Mar. 13, 2008

(65) Prior Publication Data
US 2010/0021386 A1 Jan. 28, 2010

Related U.S. Application Data

(60) Provisional application No. 60/842,983, filed on Sep. 8, 2006.

(51) Int. Cl.
*A61K 31/47* (2006.01)
*A61K 36/282* (2006.01)

(52) U.S. Cl.
CPC ............ *A61K 31/47* (2013.01); *A61K 36/282* (2013.01)

(58) Field of Classification Search
None
See application file for complete search history.

(56) References Cited

U.S. PATENT DOCUMENTS

2005/0014833 A1 1/2005 Clark et al.

FOREIGN PATENT DOCUMENTS

| FR | WO 0100603 A1 | * | 1/2001 | ............ C07D 263/32 |
|---|---|---|---|---|
| GB | 2058785 A | * | 4/1981 | .............. C07C 37/50 |
| NL | WO 2004019552 A1 | * | 3/2004 | .............. G06F 21/10 |
| WO | WO-0181348 A1 | | 11/2001 | |
| WO | WO-0202138 A1 | | 1/2002 | |
| WO | WO-2005/009437 A1 | | 2/2005 | |

OTHER PUBLICATIONS

Kono et al. in The Journal of Clinical Investigation 2000; 106(7):867-872.*
Fischer et al. In The Journal of Biological Chemistry 278(30), 27997-28004 (2003).*
Leibowitz et al. In FEBS Letters 473 (2000) 333-336.*
Tanaka et al. In Proc. Natl. Acad. Sci. USA 100(26), 15924-15929 (2003).*
Mangelsdorf et al. In Cell 83, 835-839,1995.*
S.M. Kim et al., 14 Korean Journal of Obesity, 29-38 (2005).*
J. Berger et al., 274 Journal of Biological Chemistry, 6718-6725 (1999).*
W. Colburn, Efficient and Effective Drug Development, in Applications of Pharmacokinetic Principles in Drug Development 1-20 (Rajesh Krishna ed., 2004).*
S. Takashashi et al., 53 Pharmacological Research, 501-507 (2006).*
S. Luquet et al., 1740 Biochimica et Biophysica Acta, 313-317 (2005).*
P.A. Grimaldi, 87 Biochimie, 5-8 (2005).*
S. Luquet, 86 Biochimie, 833-837 (2004).*
K. Tomita et al., Gastroenterology, 873-885 (2004).*
L. Julan et al., 146 Endocrinology, 1482-1490 (2005).*
J. Colman et al., 21 Gut, 965-969 (1980).*
G. Bock et al., 56 Diabetes, 1703-1711 (2007) ("Bock").*
M. Matsuda et al., 22 Diabetes Care, 1462-1470 (1999).*
S.B. Biddinger et al., 7 Cell Metabolism, 125-134 (2008).*
S. Bhattacharya et al., 32 Journal of Bioscience, 405-413 (2007).*
R.A. DeFronzo et al., 23 Diabetologia, 313-319 (1982).*
R.A. DeFronzo et al., 6 American Journal of Physiology, E214-E223 (1999).*
C. Cheng et al., 25 Annals of Nuclear Medicine, 755-761 (2011).*
Y Onishi et al., 303 Biochemical and Biophysical Research Communications, 788-794 (2003).*
M. Pang et al., 50 Journal of Hepatology, 1192-1201 (2009).*
Keegan et al. "Ethanol-Related Liver Injury in the Rat: A Model of Steatosis, Inflammation and Pericentral Fibrosis." *J. Hepatol.* 23.5(1995):591-600.
Crabb, "Alcohol deranges hepatic lipid metabolism via altered transcriptional regulation", *Transactions of the American Clinical and Climatological Association*, 115:273-287 (2004).
Tsutsumi et al., "Effect of fenofibrate on fatty liver in rats treated with alcohol", *Alcoholism : Clinical and Experimental Research*, 25(6):75S-79S (2001).
Hong et al., "Interleukin 6 alleviates hepatic steatosis and ischemia/reperfusion injury in mice with fatty liver disease", *Hepatology*, 40(4):933-941 (2004).
Kite et al., "Bezafibrate may attenuate biliary damage associated with chronic liver diseases accompanied by high serum biliary enzyme levels", *Journal of Gastroenterology*, 41(7):686-692 (2006).
Lee et al., "PPARdelta regulates glucose metabolism and insulin sensitivity", *Proceedings of the National Academy of Sciences of the United States of America*, 103(9):3444-3449 (2006).
Hellemans et al., "Peroxisome proliferator-activated receptor-beta signaling contributes to enhanced proliferation of hepatic stellate cells", *Gastroenterology*, 124(1):184-201 (2003).

(Continued)

*Primary Examiner* — Alexander R Pagano
(74) *Attorney, Agent, or Firm* — Mintz Levin Cohn Ferris Glovsky and Popeo, P.C.

(57) ABSTRACT

This invention relates to methods for treating, preventing, or reversing liver disease or damage produced by chronic alcohol intake by administering at least one peroxisome proliferator activated receptor (PPAR) agonist.

10 Claims, 17 Drawing Sheets

(56) References Cited

OTHER PUBLICATIONS

Yeon et al., "Potential role of PTEN phosphate in ethanol-impaired survival signaling in the liver", *Hepatology*, 38(3):703-714 (2003).
Webb et al., "Sex differences in ethanol-induced hypnosis and hypothermia in young Long-Evans rats", *Alcoholism, Clinical and Experimental Research*, 26(5):695-704 (2002).
Turmelle et al., "Rosiglitazone inhibits mouse liver regeneration", The FASEB Journal Official Publication of the Federation of American Societies for Experimental Biology, 20(14)2609-2611 (2006).
Rouach et al., "Effect of chronic ethanol feeding on lipid peroxidation and protein oxidation in relation to liver pathology", *Hepatology*, 25(2):351-355 (1997).
Duguay et al., "Inhibition of Liver Regeneration by Chronic Alcohol Administration", *Gut*, 23:8-13 (1982).
Brooks, "DNA Damage, DNA Repair, and Alcohol Toxicity-A Review", *Alcoholism: Clinical and Experimental Research*, 21(6):1073-1082 (1997).
Gouillon et al., "Inhibition of Ethanol-Induced Liver Disease in the Intragastric Feeding Rat Model by Chlormethiazole", *Experimental Biology and Medicine*, 224(4):302-308 (2000).
Yamamoto et al., "Mechanism of enhanced lipid peroxidation in the liver of Long-Evans cinnamon (LEC) rats", *Molecular Toxicology*, 73:457-464 (1999).
Etkind et al., "Cocaine and Alcohol Synergism in Taste Aversion Learning", *Pharmacology Biochemistry and Behavior*, 59(3):649-655 (1998).
Nakajima et al., "Peroxisome Proliferator-Activated Receptor alpha Protects Against Alcohol-Induced Liver Damage", *Hepatology*, 4(20):972-989 (2004).
Akerman et al., "Long-term Ethanol Consumption Alters the Hepatic Response to the Regenerative Effects of Tumor Necrosis Factor-α", *Hepatol.*, 17:1066-1073 (1993).
Avruch, J., "Insulin signal transduction through protein kinase cascades", *Mol. Cell. Biochem.*, 182:31-48 (1998).
Backer et al., "Phosphatidylinositol 3'-kinase is activated by association with IRS-1 during insulin stimulation", *EMBO J.*, 11(9):3469-3479 (1992).
Benedetti et al., "Subcellular changes and apoptosis induced by ethanol in rat liver", *J. Hepatol.*, 6:137-143 (1988).
Brunet et al., "Transcription-dependent and -independent control of neuronal survival by the PI3K-Akt signaling pathway", *Curr. Opin. Neurobiol.*, 11:297-305 (2001).
Burgering et al., "Protein kinase B (c-Akt) in phosphatidylinositol-3-OH kinase signal transduction", *Nature*, 376:599-602 (1995).
Carpenter et al., "Phospholipase C-γ as a Signal-Transducing Element", *Exp. Cell Res.*, 253:15-24 (1999).
Carpenter et al., "A Tightly Associated Serine/Threonine Protein Kinase Regulates Phosphoinositide 3-Kinase Activity", *Mol. Cell. Biol.*, 13(3):1657-1665 (1993).
Carter et al., "Ethanol-induced Inhibition of Liver Cell Function: I. Effect of Ethanol on Hormone Stimulated Hepatocyte DNA Synthesis and the Role of Ethanol Metabolism", *Alcohol Clin. Exp. Res.*, 12(4):555-562 (1988).
Carter et al., "Ethanol Inhibits Hormone Stimulated Hepatocyte DNA Synthesis", *Biochem Biophys. Res. Commun.*, 128:767-774 (1985).
Castaneda et al., "Apoptosis induced in HepG2 cells by short exposure to millimolar concentrations of ethanol involves the Fas-receptor pathway", *J. Cancer Res. Clin. Oncol.*, 127:418-424 (2001).
Chaudhary et al., "Phosphatidylinositol 3-kinase regulates Raf1 through Pak phosphorylation of serine 338", *Curr. Biol.*, 10:551-554 (2000).
Chen et al., "Effects of ethanol on mitogen-activated protein kinase and stress-activated protein kinase cascades in normal and regenerating liver", *Biochem. J.*, 334:669-676 (1998).
Comer et al., "PI 3-Kinases and PTEN: How Opposites Chemoattract", *Cell*, 109:541-544 (2002).

Cross et al., "Inhibition of glycogen synthase kinase-3 by insulin mediated by protein kinase B", *Nature*, 378:785-789 (1995).
Dahia et al., "*PTEN* is inversely correlated with the cell survival factor Akt/PKB and is inactivated via multiple mechanisms in haematological malignancies", *Hum. Mol. Genet.*, 8(2):185-193 (1999).
Deaciuc et al., "Modulation of Caspase-3 Activity and Fas Ligand mRNA Expression in Rat Liver Cells In Vivo by Alcohol and Lipopolysaccharide", *Alcohol Clin. Exp. Res.*, 23:349 (1999).
Deaciuc et al., "Chronic alcohol exposure of rats exacerbates apoptosis in hepatocytes and sinusoidal endothelial cells", *Hepatol. Res.*, 19:306-324 (2001).
Dhand et al., "PI 3-kinase: structural and functional analysis of intersubunit interactions", *EMBO J.*, 13(3):511-521 (1994).
Diehl et al., "Recent Events in Alcoholic Liver Disease V. Effects of ethanol on liver regeneration", *Am. J. Physiol. Gastrointest. Liver Physiol.*, 288:G1-G6 (2005).
Diehl et al., "Regulation of signal transduction during liver regeneration", *Faseb J.*, 10:215-227 (1996).
Diehl et al., "Ethanol Inhibits Liver Regeneration in Rats Without Reducing Transcripts of Key Protooncogenes", *Gastroenterol.*, 99:1105-1112 (1990).
Diehl et al., "Chronic Ethanol Consumption Disturbs G-Protein Expression and Inhibits Cyclic AMP-dependent Signaling in Regenerating Rat Liver", *Hepatol.*, 16:1212-1219 (1992).
Diehl, A. M., "Effect of Ethanol on Tumor Necrosis Factor Signaling During Liver Regeneration", *Clin Biochem.*, 32(7):571-578 (1999).
Dudek et al., "Regulation of Neuronal Survival by the Serine-Threonine Protein Kinase Akt", *Science*, 275:661-665 (1997).
Eves et al., "Akt, a Target of Phosphatidylinositol 3-Kinase, Inhibits Apoptosis in a Differentiating Neuronal Cell Line", *Mol. Cell. Biol.*, 18(4):2143-2152 (1998).
Fausto, N., "Liver regeneration", *J Hepatol.*, 32:19-31 (2000).
Franke et al., "The Protein Kinase Encoded by the *Akt* Proto-Oncogene Is a Target of the PDGF-Activated Phosphatidylinositol 3-Kinase", *Cell*, 81:727-736 (1995).
Franke et al., "PI3K: Downstream AKTion Blocks Apoptosis", *Cell*, 88:435-437 (1997).
Goldin et al., "Apoptotic Bodies in a Murine Model of Alcoholic Liver Disease: Reversibility of Ethanol-Induced Changes", *J. Pathol.*, 171:73-76 (1993).
Gustafson et al., "Phosphotyrosine-Dependent Interaction of SHC and Insulin Receptor Substrate 1 with the NPEY Motif of the Insulin Receptor via a Novel Non-SH2 Domain", *Mol. Cell. Biol.*, 15(5):2500-2508 (1995).
Harada et al., "Phosphorylation and Inactivation of BAD by Mitochondria-Anchored Protein Kinase A", *Mol. Cell*, 3:413-422 (1999).
Harlan et al., "Pleckstrin homology domains bind to phosphatidylinositol 4,5-bisphosphate", *Nature*, 371:168-170 (1994).
Higashi et al., "Ethanol Causes Desensitization of Receptor-mediated Phospholipase C Activation in Isolated Hepatocytes", *J. Biol. Chem.*, 266(4):2178-2190 (1991).
Higuchi et al., "The Mitochondrial Permeability Transition Contributes to Acute Ethanol-Induced Apoptosis in Rat Hepatocytes", *Hepatol.*, 34:320-328 (2001).
Hoek et al., "Ethanol and signal transduction in the liver", *FASEB J.*, 6:2386-2396 (1992).
Ito et al., "Overexpression of Human Insulin Receptor Substrate 1 Induces Cellular Transformation with Activation of Mitogen-Activated Protein Kinases", *Mol. Cell. Biol.*, 16(3):943-951 (1996).
Kandel et al., The Regulation and Activities of the Multifunctional Serine/Threonine Kinase Akt/Pkb, *Exp. Cell Res.*, 253:210-229 (1999).
Khamzina et al., "Correlation of α-Fetoprotein Expression in Normal Hepatocytes during Development with Tyrosine Phosphorylation and Insulin Receptor Expression", *Mol. Biol. Cell*, 9:1093-1105 (1998).
Le Good et al., "Protein Kinase C Isotypes Controlled by Phosphoinositide 3-Kinase Through the Protein Kinase PDK1", *Science*, 281:2042-2045 (1998).

(56) References Cited

OTHER PUBLICATIONS

Leslie et al., "PTEN: The down side of PI 3-kinase signalling",*Cell Signal.*, 14:285-295 (2002).
Li et al., "TEP1, Encoded by a Candidate Tumor Suppressor Locus, Is a Novel Protein Tyrosine Phosphatase Regulated by Transforming Growth Factorβ", *Cancer Res.*, 57:2124-2129 (1997).
Maehama et al., "PTEN and Myotubularin: Novel Phosphoinositide Phosphatases", *Annu. Rev. Biochem.*, 70:247-279 (2001).
Maehama et al., "PTEN: a tumour suppressor that functions as a phospholipid phosphatase", *Trends Cell. Biol.*, 9:125-128 (1999).
Michalopoulos et al., "Liver Regeneration", *Science*, 276:60-66 (1997).
Musacchio et al., "The PH domain: a common piece in the structural patchwork of signalling proteins", *Trends Biochem. Sci.*, 18:343-348 (1993).
Myers et al., "IRS-1 activates phosphatidylinositol 3'-kinase by associating with src homology 2 domains of p85", *Proc. Natl. Acad. Sci. U.S.A.*, 89:10350 (1992).
Nanji, A. A., "Apoptosis and Alcoholic Liver Disease", *Semin. Liver Dis.*, 18(2):187-190 (1998).
Natori et al, "Hepatocyte apoptosis is a pathologic feature of human alcoholic hepatitis", *J. Hepatol.*, 34:248-253 (2001).
Nishiyama et al., "Cloning and Increased Expression of an Insulin Receptor Substrate—1-Like Gene in Human Hepatocellular Carcinoma", *Biochem. Biophys. Res. Commun.*, 183(1):280-285 (1992).
Pap et al., "Role of Glycogen Synthase Kinase-3 in the Phosphatidylinositol 3-Kinase/Akt Cell Survival Pathway", *J. Biol. Chem.*, 273(32):19929-19932 (1998).
Pistoi et al., "Prometheus' myth revisited: transgenic mice as a powerful tool to study liver regeneration", *Faseb J.*, 10:819828 (1996).
Platanias et al., "The Type I Interferon Receptor Mediates Tyrosine Phosphorylation of Insulin Receptor Substrate 2", *J. Biol. Chem.*, 271(1):278-282 (1996).
Rose et al., "Insulin receptor substrate 1 is required for insulin-mediated mitogenic signal transduction", *Proc. Natl. Acad. Sci. U.S.A.*, 91:797-801 (1994).
Sasaki et al., "Ethanol Impairs Insulin Receptor Substrate-1 Mediated Signal Transduction During Rat Liver Regeneration", *Biochem. Biophys. Res. Commun.*, 199(1):403-409 (1994).
Sasaki et al., "Expression and Phosphorylation of Insuling Receptor Substrate 1 during Rat Liver Regeneration", *J Biol. Chem.*, 268(6):3805-3808 (1993).
Saso et al., "Inhibitory Effect of Ethanol on Hepatocyte Growth Factor-induced DNA Synthesis and $Ca^{2+}$ Mobilization in Rat Hepatocytes", *Alcohol Clin. Exp. Res.*, 20(9):330A-334A (1996).
Saso et al., "Differential Inhibition of Epidermal Growth Factor Signaling Pathways in Rat Hepatocytes by Long-term Ethanol Treatment", *Gastroenterol.*, 112:2073-2088 (1997).
Sekiya et al., "Regulation of phospholipase C isozymes: activation of phospholipase C-γ in the absence of tyrosine-phosphorylation", *Chem. Phys. Lipids*, 98:3-11 (1999).
Seminario et al., "Signaling pathways of D3-phosphoinositide-binding kinases in T cells and their regulation by PTEN", *Semin. Immunol.*, 14:27-36 (2002).
Skolnik et al., "The Function of GRB2 in Linking the Insulin Receptor to Ras Signaling Pathways", *Science*, 260:1953-1955 (1993).
Sohn et al., "Neuritic sprouting with aberrant expression of the nitric oxide synthase III gene in neurodegenerative diseases", *J. Neurol Sci.*, 162:133-151 (1999).
Srivastava et al., "Potential mechanism(s) involved in the regulation of glycogen synthesis by insulin", *Mol. Cell. Biochem.*, 182:135-141 (1998).
Suhara et al., "Suppression of Akt Signaling Induces Fas Ligand Expression: Involvement of Caspase and Jun Kinase Activation in Akt-Mediated Fas Ligand Regulation", *Mol. Cell. Biol.*, 22:680-691 (2002).

Sun et al., Pleiotropic Insulin Signals Are Engaged by Multisite Phosphorylation of IRS-1, *Mol. Cell. Biol.*, 13(12):7418-7428 (1993).
Sun et al., "The IRS-2 Gene on Murine Chromosome 8 Encodes a Unique Signaling Adapter for Insulin and Cytokine Action", *Mol. Endocrinol.*, 11:251-262 (1997).
Sun et al., "Structure of the insulin receptor substrate IRS-1 defines a unique signal transduction protein", *Nature*, 352:73-77 (1991).
Sun et al., "Role of IRS-2 in insuling and cytokine signalling", *Nature*, 377:173-177 (1995).
Tanaka et al., "Insulin Receptor Substrate 1 Overexpression in Human Hepatocellular Carcinoma Cells Prevents Transforming Growth Factor β1-induced Apoptosis", *Cancer Res.*, 56:3391-3394 (1996).
Tanaka et al., "Biological Effects of Human Insulin Receptor Substrate-1 Overexpression in Hepatocytes", *Hepatol.*, 26:598-604 (1997).
Tanaka et al., "Neoplastic Transformation Induced by Insulin Receptor Substrate-1 Overexpression Requires an Interaction with Both Grb2 and Syp Signaling Molecules", *J. Biol. Chem.*, 271(24):14610-14616 (1996).
Tanaka et al., "Biologic significance of angiopoietin-2 expression in human hepatocellular carcinoma", *J. Clin. Invest.*, 103:341-345 (1999).
Tanaka et al., "A Carboxy-terminal Truncated Insulin Receptor Substrate-1 Dominant Negative Protein Reverses the Human Hepatocellular Carcinoma Malignant Phenotype", *J. Clin. Invest.*, 98:2100-2108 (1996).
Torres et al., "The Tumor Suppressor PTEN Is Phosphorylated by the Protein Kinase CK2 at Its C Terminus", *J. Biol. Chem.*, 276:993-998 (2001).
Touhara et al., "Binding of G Protein βα-Subunits to Pleckstrin Homology Domains", *J. Biol. Chem.*, 269(14):10217-10220 (1994).
Wands et al., "Inhibition of Hepatic Regeneration in Rats by Acute and Chronic Ethanol Intoxication", *Gastroenterol.*, 77:528-531 (1979).
Waters et al., "Functional Expression of Insulin Receptor Substrate-1 Is Required for Insulin-stimulated Mitogenic Signaling", *J. Biol. Chem.*, 268(30):22231-22234 (1993).
Weng et al., "PTEN inhibits insulin-stimulated MEK/MAPK activation and cell growth by blocking IRS-1 phosphorylation and IRS-1/Grb-2/Sos complex formation in a breast cancer model", *Hum. Mol. Genet.*, 10(6):605-616 (2001).
White, M. F., "The IRS-Signaling System: A Network of Docking Proteins That Mediate Insulin and Cytokine Action", *Recent Prog. Horm. Res.*, 53:119-138 (1998).
Yamada et al., "Tumor suppressor PTEN: modulator of cell signaling, growth, migration and apoptosis", *J. Cell Sci.*, 114:2375-2382 (2001).
Zha et al., "Serine Phosphorylation of Death Agonist BAD in Response to Survival Factor Results in Binding to 14-3-3 Not BCL-$X_L$", *Cell*, 87:619-628 (1996).
Zhang et al., "Specific involvement of $G_{\alpha i2}$ with epidermal growth factor receptor signaling in rat hepatocytes, and the inhibitory effect of chronic ethanol", *Biochem. Pharmacol.*, 61:1021-1027 (2001).
Zhang et al., "Chronic Ethanol Administration to Rats Decreases Receptor-operated Mobilization of Intracellular Ionic Calcium in Cultured Hepatocytes and Inhibits 1,4,5-inositol Trisphosphate Production: Relevance to Impaired Liver Regeneration", *J. Clin. Invest.*, 98:1237-1244 (1996).
Zheng et al., "Activation of Phosphoinositide 3-Kinase Activity by Cdc42Hs Binding to p85", *J. Biol. Chem.*, 269(29):18727-18730 (1994).
Zhou et al., "Ethanol-Induced Apoptosis in Mouse Liver. Fas- and Cytochrome c-Mediated Caspase-3 Activation Pathway", *Am. J. Pathol.*, 159(1):329-338 (2001).

\* cited by examiner

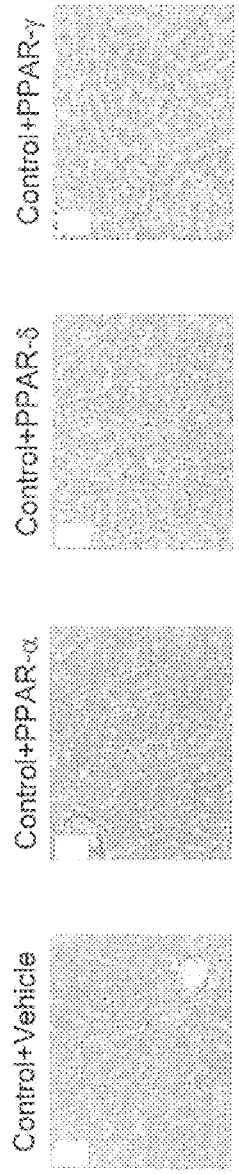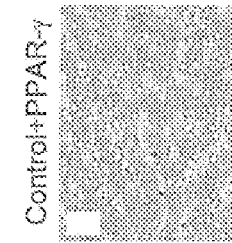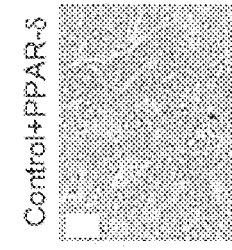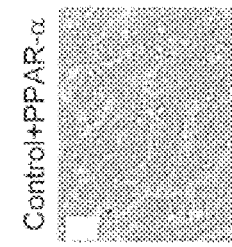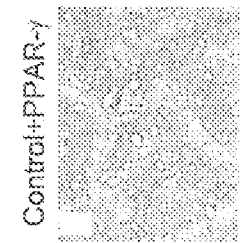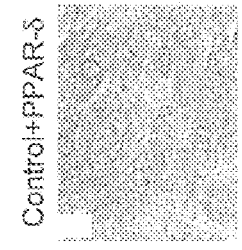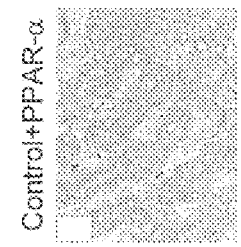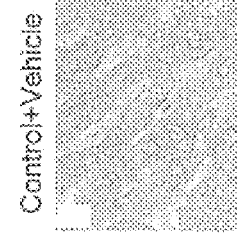

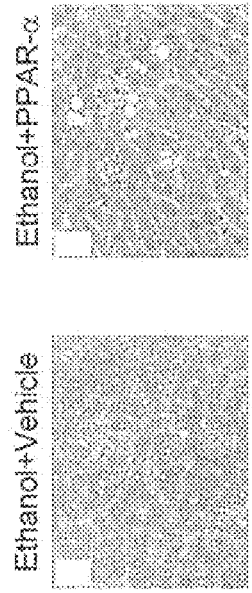
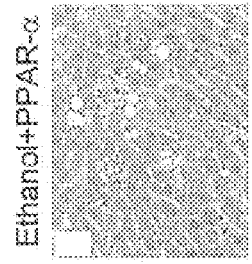
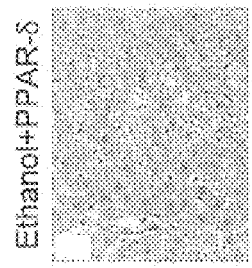
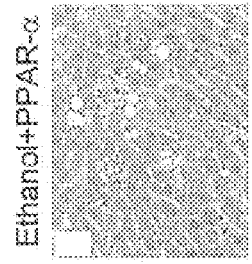
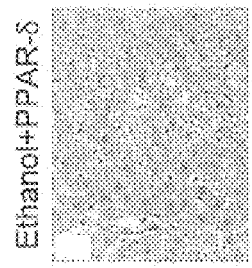
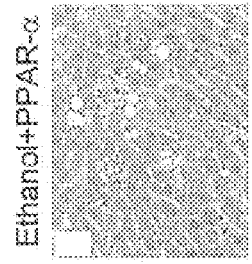
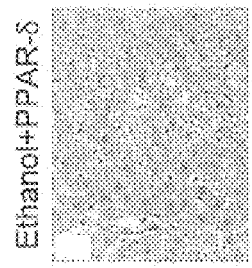
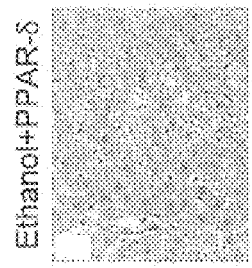

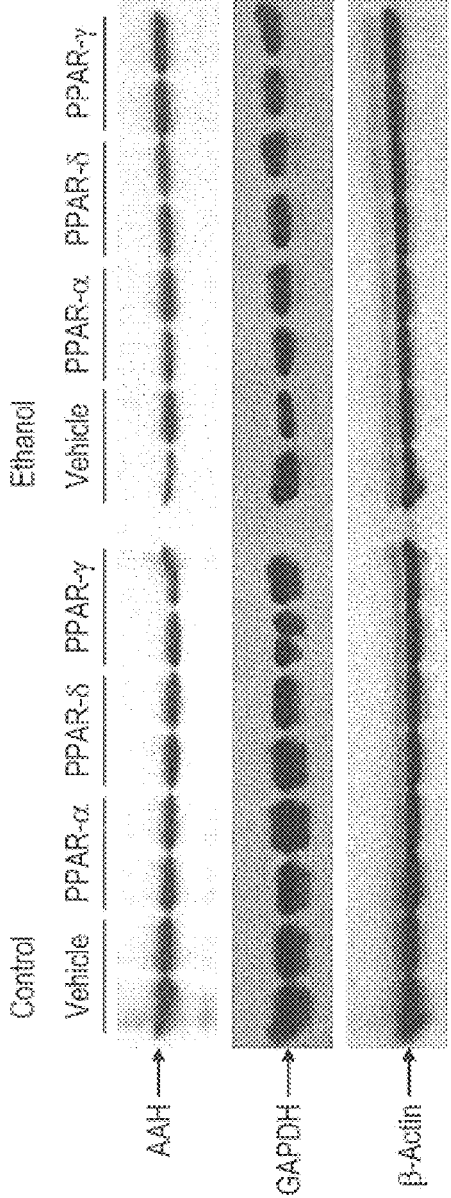
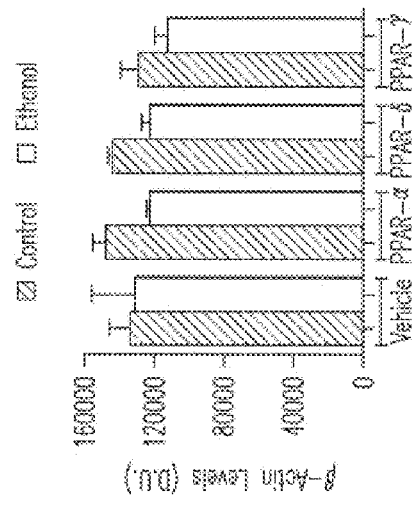
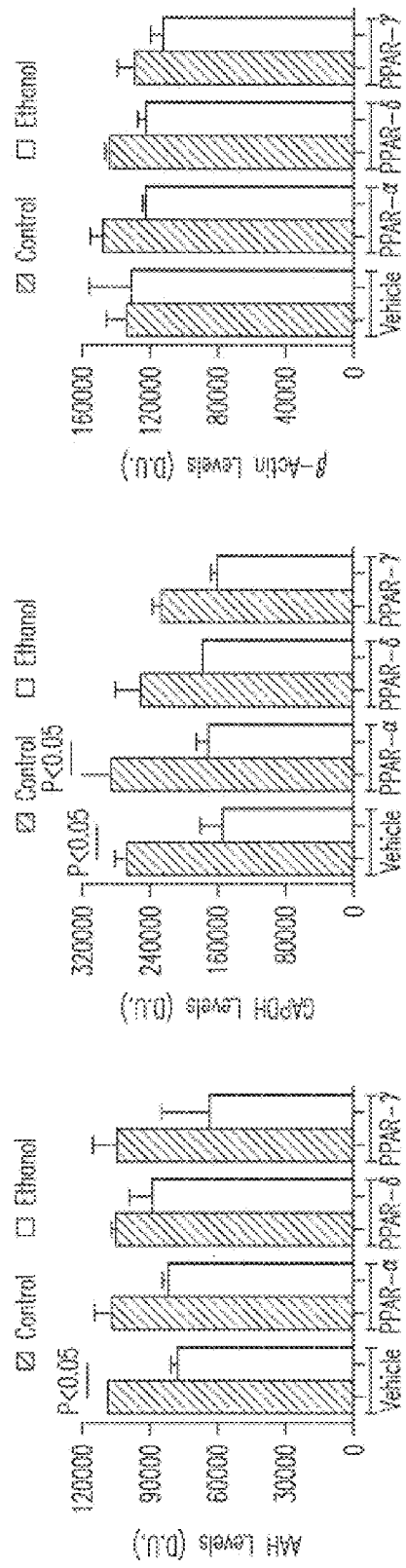
FIG. 16A
FIG. 16B
FIG. 16C
FIG. 16D

SEQUENCE LISTING

```
<160> NUMBER OF SEQ ID NOS: 36

<210> SEQ ID NO 1
<211> LENGTH: 20
<212> TYPE: DNA
<213> ORGANISM: Artificial Sequence
<220> FEATURE:
<223> OTHER INFORMATION: Synthetic 18S rRNA primer

<400> SEQUENCE: 1
ggacacggac aggattgaca                                                   20

<210> SEQ ID NO 2
<211> LENGTH: 20
<212> TYPE: DNA
<213> ORGANISM: Artificial Sequence
<220> FEATURE:
<223> OTHER INFORMATION: Synthetic 18S rRNA primer

<400> SEQUENCE: 2
acccacggaa tcgagaaaga                                                   20

<210> SEQ ID NO 3
<211> LENGTH: 22
<212> TYPE: DNA
<213> ORGANISM: Artificial Sequence
<220> FEATURE:
<223> OTHER INFORMATION: Synthetic insulin primer

<400> SEQUENCE: 3
ttctacacac ccaagtcccg tc                                                22

<210> SEQ ID NO 4
<211> LENGTH: 22
<212> TYPE: DNA
<213> ORGANISM: Artificial Sequence
<220> FEATURE:
<223> OTHER INFORMATION: Synthetic insulin primer

<400> SEQUENCE: 4
atccacaatg ccacgcttct gc                                                22

<210> SEQ ID NO 5
<211> LENGTH: 22
<212> TYPE: DNA
<213> ORGANISM: Artificial Sequence
<220> FEATURE:
<223> OTHER INFORMATION: Synthetic insulin receptor primer

<400> SEQUENCE: 5
tgacaatgag gaatgtgggg ac                                                22

<210> SEQ ID NO 6
<211> LENGTH: 24
<212> TYPE: DNA
<213> ORGANISM: Artificial Sequence
```

```
<220> FEATURE:
<223> OTHER INFORMATION: Synthetic insulin receptor primer

<400> SEQUENCE: 6
gggcaaactt tctgacaatg actg                                          24

<210> SEQ ID NO 7
<211> LENGTH: 23
<212> TYPE: DNA
<213> ORGANISM: Artificial Sequence
<220> FEATURE:
<223> OTHER INFORMATION: Synthetic IGF-I primer

<400> SEQUENCE: 7
gaccaagggg cttttacttc aac                                           23

<210> SEQ ID NO 8
<211> LENGTH: 22
<212> TYPE: DNA
<213> ORGANISM: Artificial Sequence
<220> FEATURE:
<223> OTHER INFORMATION: Synthetic IGF-I primer

<400> SEQUENCE: 8
tttgtaggct tcagcggagc ac                                            22

<210> SEQ ID NO 9
<211> LENGTH: 23
<212> TYPE: DNA
<213> ORGANISM: Artificial Sequence
<220> FEATURE:
<223> OTHER INFORMATION: Synthetic IGF-I receptor primer

<400> SEQUENCE: 9
gaagtctgcg gtggtgataa agg                                           23

<210> SEQ ID NO 10
<211> LENGTH: 22
<212> TYPE: DNA
<213> ORGANISM: Artificial Sequence
<220> FEATURE:
<223> OTHER INFORMATION: Synthetic IGF-I receptor primer

<400> SEQUENCE: 10
tctgggcaca aagatggagt tg                                            22

<210> SEQ ID NO 11
<211> LENGTH: 22
<212> TYPE: DNA
<213> ORGANISM: Artificial Sequence
<220> FEATURE:
<223> OTHER INFORMATION: Synthetic IGF-II primer

<400> SEQUENCE: 11
ccaagaagaa aggaagggga cc                                            22

<210> SEQ ID NO 12
<211> LENGTH: 22
<212> TYPE: DNA
<213> ORGANISM: Artificial Sequence
<220> FEATURE:
<223> OTHER INFORMATION: Synthetic IGF-II primer

<400> SEQUENCE: 12
ggcggctatt gttgttcaca gc                                            22
```

<210> SEQ ID NO 13
<211> LENGTH: 24
<212> TYPE: DNA
<213> ORGANISM: Artificial Sequence
<220> FEATURE:
<223> OTHER INFORMATION: Synthetic IGF-II receptor primer

<400> SEQUENCE: 13
ttgctattga ccttagtccc ttgg                                          24

<210> SEQ ID NO 14
<211> LENGTH: 24
<212> TYPE: DNA
<213> ORGANISM: Artificial Sequence
<220> FEATURE:
<223> OTHER INFORMATION: Synthetic IGF-II receptor primer

<400> SEQUENCE: 14
agagtgagac ctttgtgtcc ccac                                          24

<210> SEQ ID NO 15
<211> LENGTH: 20
<212> TYPE: DNA
<213> ORGANISM: Artificial Sequence
<220> FEATURE:
<223> OTHER INFORMATION: Synthetic albumin primer

<400> SEQUENCE: 15
cttcaaagcc tgggcagtag                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic albumin primer

<400> SEQUENCE: 16
tggagatagt ggcctggttc                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic ASBT primer

<400> SEQUENCE: 17
gcattggcat ttctctggtt                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic ASBT primer

<400> SEQUENCE: 18
ggttcaatga tccaggcact                                               20

<210> SEQ ID NO 19
<211> LENGTH: 20
<212> TYPE: DNA
<213> ORGANISM: Artificial Sequence
<220> FEATURE:
<223> OTHER INFORMATION: Synthetic KCR primer

```
<400> SEQUENCE: 19
tcacaaatgc tgtggaccat                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic KCR primer

<400> SEQUENCE: 20
gtcttcacgc tctccgtttc                                               20

<210> SEQ ID NO 21
<211> LENGTH: 20
<212> TYPE: DNA
<213> ORGANISM: Artificial Sequence
<220> FEATURE:
<223> OTHER INFORMATION: Synthetic GFAP primer

<400> SEQUENCE: 21
ggtggagagg gacaatctca                                               20

<210> SEQ ID NO 22
<211> LENGTH: 20
<212> TYPE: DNA
<213> ORGANISM: Artificial Sequence
<220> FEATURE:
<223> OTHER INFORMATION: Synthetic GFAP primer

<400> SEQUENCE: 22
ctcgaacttc ctcctcatgg                                               20

<210> SEQ ID NO 23
<211> LENGTH: 20
<212> TYPE: DNA
<213> ORGANISM: Artificial Sequence
<220> FEATURE:
<223> OTHER INFORMATION: Synthetic desmin primer

<400> SEQUENCE: 23
acctgcgaga ttgatgctct                                               20

<210> SEQ ID NO 24
<211> LENGTH: 19
<212> TYPE: DNA
<213> ORGANISM: Artificial Sequence
<220> FEATURE:
<223> OTHER INFORMATION: Synthetic desmin primer

<400> SEQUENCE: 24
acatccaagg ccatcttca                                                19

<210> SEQ ID NO 25
<211> LENGTH: 20
<212> TYPE: DNA
<213> ORGANISM: Artificial Sequence
<220> FEATURE:
<223> OTHER INFORMATION: Synthetic colla2 primer

<400> SEQUENCE: 25
acctcagggt gttcaaggtg                                               20

<210> SEQ ID NO 26
```

```
<211> LENGTH: 20
<212> TYPE: DNA
<213> ORGANISM: Artificial Sequence
<220> FEATURE:
<223> OTHER INFORMATION: Synthetic col1a2 primer

<400> SEQUENCE: 26
cggattccaa taggaccaga                                                     20

<210> SEQ ID NO 27
<211> LENGTH: 22
<212> TYPE: DNA
<213> ORGANISM: Artificial Sequence
<220> FEATURE:
<223> OTHER INFORMATION: Synthetic IRS-1 primer

<400> SEQUENCE: 27
gataccgatg gcttctcaga cg                                                  22

<210> SEQ ID NO 28
<211> LENGTH: 23
<212> TYPE: DNA
<213> ORGANISM: Artificial Sequence
<220> FEATURE:
<223> OTHER INFORMATION: Synthetic IRS-1 primer

<400> SEQUENCE: 28
tcgttctcat aatactccag gcg                                                 23

<210> SEQ ID NO 29
<211> LENGTH: 23
<212> TYPE: DNA
<213> ORGANISM: Artificial Sequence
<220> FEATURE:
<223> OTHER INFORMATION: Synthetic IRS-2 primer

<400> SEQUENCE: 29
caacattgac tttggtgaag ggg                                                 23

<210> SEQ ID NO 30
<211> LENGTH: 24
<212> TYPE: DNA
<213> ORGANISM: Artificial Sequence
<220> FEATURE:
<223> OTHER INFORMATION: Synthetic IRS-2 primer

<400> SEQUENCE: 30
tgaagcagga ctactggctg agag                                                24

<210> SEQ ID NO 31
<211> LENGTH: 24
<212> TYPE: DNA
<213> ORGANISM: Artificial Sequence
<220> FEATURE:
<223> OTHER INFORMATION: Synthetic IRS-4 primer

<400> SEQUENCE: 31
acctgaagat aagggtcgt ctgc                                                 24

<210> SEQ ID NO 32
<211> LENGTH: 22
<212> TYPE: DNA
<213> ORGANISM: Artificial Sequence
<220> FEATURE:
<223> OTHER INFORMATION: Synthetic IRS-4 primer

<400> SEQUENCE: 32
```

-continued

```
tgtgtggggt ttagtggtct gg                                              22

<210> SEQ ID NO 33
<211> LENGTH: 21
<212> TYPE: DNA
<213> ORGANISM: Artificial Sequence
<220> FEATURE:
<223> OTHER INFORMATION: Synthetic GAPDH primer

<400> SEQUENCE: 33
agtgggcatc aatggatttg g                                               21

<210> SEQ ID NO 34
<211> LENGTH: 23
<212> TYPE: DNA
<213> ORGANISM: Artificial Sequence
<220> FEATURE:
<223> OTHER INFORMATION: Synthetic GAPDH primer

<400> SEQUENCE: 34
ggggatttcc ttaggttctt tgc                                             23

<210> SEQ ID NO 35
<211> LENGTH: 21
<212> TYPE: DNA
<213> ORGANISM: Artificial Sequence
<220> FEATURE:
<223> OTHER INFORMATION: Synthetic AAH primer

<400> SEQUENCE: 35
tgcctgctcg tcttgtttgt g                                               21

<210> SEQ ID NO 36
<211> LENGTH: 21
<212> TYPE: DNA
<213> ORGANISM: Artificial Sequence
<220> FEATURE:
<223> OTHER INFORMATION: Synthetic AAH Primer

<400> SEQUENCE: 36
atccgttctg taacccgttg g                                               21
```

TREATMENT, PREVENTION, AND REVERSAL OF ALCOHOL-INDUCED LIVER DISEASE

RELATED APPLICATIONS

This application is a national stage application, filed under 35 U.S.C. §371, of International Application No. PCT/US2007/019610, filed on Sep. 10, 2007, which claims the benefit of U.S. Ser. No. 60/842,983 filed Sep. 8, 2006.

BACKGROUND OF THE INVENTION

Field of the Invention

This invention is in the field of medical therapy. In particular, the invention relates to methods for treating, preventing, or reversing liver disease or damage produced by chronic alcohol intake by administering at least one peroxisome proliferator activated receptor (SPAR) agonist.

Related Art

There is increasing evidence that ethanol desensitizes hepatocytes to the trophic actions of growth factors and cytokine networks. Indeed, rat hepatocytes exposed to ethanol in culture have a markedly reduced response to insulin and epidermal growth factor (EGF) stimulated DNA synthesis. Thus, short- and long-term ethanol exposure impairs hepatocyte DNA synthesis in vitro (Carter et al., Biochem. Biophys. Res. Commun. 128:767 (1985); Carter et al., Alcohol Clin. Exp. Res. 12:555 (1988)) and the ability of the liver to regenerate after partial hepatectomy (Diehl et al., Gastroenterology 99:1105 (1990); Diehl et al., Hepatology 16:1212 (1992); Wands et al., Gastroenterology 77:528 (1979)). The precise molecular mechanism(s) by which ethanol inhibits hepatocyte proliferation are poorly understood. Liver regeneration is regulated by several growth factors and cytokines of which tumor necrosis factor (TNF)-α, EGF, transforming growth factor alpha (TGF-α), interleukin (IL)-6, hepatocyte growth factor (HGF), and insulin are believed to be most important (Michalopoulos et al., Science 276:60 (1997); Pistoi et al., FASEB J. 10:819 (1996); Fausto, J. Hepatol. 32:19 (2000). In this regard, previous studies suggested that ethanol interferes with signal transduction cascades activated by HGF (Saso et al., Alcohol Clin. Exp. Res. 20:330A (1996)), EGF (Zhang et al., J. Clin. Invest. 98:1237 (1996); Higashi et al., J. Biol. Chem. 266: 2178 (1991); Saso et al., Gastroenterology 112:2073 (1997)), or TNF-α (Akerman et al., Hepatology 17:1066 (1993)) and with $Ca^{2+}$-mediated signals in hepatocytes (Sun et al., Mol. Endocrinol. 11:251 (1997)). Furthermore, chronic ethanol consumption disturbs G-protein expression and inhibits cyclic AMP-dependent signaling in regenerating rat liver (Diehl et al., FASEB J. 10:215 (1996); Hoek et al., FASEB J. 6:2386 (1992)). Other signal transduction pathways are also adversely influenced by in vivo exposure to ethanol, as shown by several investigators. For example, G protein coupling to the EGF receptor is impaired (Zhang et al., Biochem. Pharmacol. 61:1021 (2001)); TNF-α-induced expression of NFκβ and JNK following partial hepatectomy is altered (Diehl, Clin. Biochem. 32:571 (1999)); and activation of p42/44, MAPK, p38 MAPK and JNK is reduced by acute or chronic ethanol exposure (Chen et al., Biochem. J. 334-669 (1998)).

Since hepatocyte growth factors such as EGF, TGF-α, HGF, and insulin activate receptor tyrosine kinases, the effects of ethanol on signal transduction as mediated through tyrosine phosphorylation of their intracellular substrates have been examined. Previous work established the biologic relevance of this pathway since ethanol is a potent inhibitor of DNA synthesis (Carter et al., Biochem. Biophys. Res. Commun. 128:767 (1985); Diehl et al., Gastroenterology 99:1105 (1990); Wands et al., Gastroenterology 77:528 (1979); Duguay et al., Gut 23:8 (1982)), and both insulin (Sasaki et al., Biochem. Biophys. Res. Commun. 199:403 (1994)) and cyclic AMP-mediated signal transduction (Diehl et al., Hepatology 16:1212 (1992)). These effects of ethanol may be mediated by uncoupling of insulin signal transduction pathways that are involved in mitogenesis (Sasaki et al., Biochem. Biophys. Res. Commun. 199:403 (1994)). Indeed, IRS-1-mediated signaling plays a critical role in regulating hepatocyte growth in the adult liver (Ito et al., Mol. Cell. Biol. 16:943 (1996); Nishiyama et al., Biochem. Biophys. Res. Commun. 183:280 (1992); Sasaki et al., J. Biol. Chem. 268:3805 (1993); Tanaka et al., J. Biol. Chem. 271:14610 (1996); Tanaka et al. Hepatology 26:598 (1997); Tanaka et al., Cancer Res. 56:3391 (1996); Tanaka et al., J. Clin. Invest. 98:2100 (1996)). It has been demonstrated in a transgenic (Tg) mouse model in which IRS-1 was overexpressed under the control of an albumin promoter, liver mass was 20-30% greater in the Tg mice relative to the non-Tg control mice, and that this difference was maintained throughout adult life (Tanaka et al. Hepatology 26:598 (1997)). This effect of IRS-1-overexpression was associated with increased hepatocyte DNA synthesis, and constitutive activation of the PI3K and Ras/Erk MAPK cascades. In other models, expression of antisense IRS-1 RNA or microinjection of IRS-1 antibodies inhibited insulin-stimulated DNA synthesis and growth (Rose et al., Proc. Natl. Acad. Sci. USA 91:797 (1994); Waters et al., J. Biol. Chem. 268:22231 (1993)). Similarly, a dominant/negative IRS-1 mutant was found to block insulin and IGF-I stimulated cell proliferation (Tanaka et al., J. Clin. Invest. 98:2100 (1996)). Furthermore, recent investigations demonstrated that activation of signaling through IRS-1 is essential for DNA synthesis and cell cycle progression, and that IRS-1 has a direct role in cellular transformation (Ito et al., Mol. Cell. Biol. 16:943 (1996); Tanaka et al., J. Biol. Chem. 271:14610 (1996); Tanaka et al., Cancer Res. 56:3391 (1996); Tanaka et al., J. Clin. Invest. 98:2100 (1996)). The effects of IRS-1 overexpression on cell growth seem to depend on constitutive activation of the mitogenic signal transduction cascades (Ito et al., Mol. Cell. Biol. 16:943 (1996); Nishiyama et al., Biochem. Biophys. Res. Commun. 183:280 (1992); Sasaki et al., J. Biol. Chem. 268:3805 (1993); Tanaka et al., J. Biol. Chem. 271:14610 (1996); Tanaka et al. Hepatology 26:598 (1997); Tanaka et al., Cancer Res. 56:3391 (1996); Tanaka et al., J. Clin. Invest. 98:2100 (1996)). Taken together these studies emphasize the importance of insulin/IGF-I signaling in liver growth and the potential adverse effect of insulin resistance on the hepatic repair process.

Insulin, a well-known hepatotrophic factor, acts through the insulin receptor (IR) to play an important role in liver growth and metabolism (Khamzina et al., Mol. Biol. Cell 9:1093 (1998); White, Recent Prog. Horm. Res. 53:119 (1998)). Upon binding to the IRα-subunit, the IRβ-subunit is autophosphorylated on tyrosyl residues, resulting in enhanced receptor tyrosyl kinase activity (White, Recent Prog. Horm. Res. 53:119 (1998)). IRS-1 is a major intracellular substrate for IR tyrosine kinase (Sun et al., Nature 352:73 (1991)). Tyrosyl-phosphorylated motifs located within the C-terminal region of IRS-1 protein (Myers et al., Trends Biochem. Sci. 19:289 (1994)) transmit signals downstream through interactions with SH2-containing molecules, including the p85 regulatory subunit of phosphatidylinositol 3'-kinase (PI3K) (Backer et al., EMBO J. 11:3469 (1992);

Myers et al., *Proc. Natl. Acad. Sci. USA* 89:10350 (1992)), growth factor receptor-bound protein 2 (Grb2) (Skolnik et al., *Science* 260:1953 (1993)), phospholipase Cβ (PLCγ) (White, *Recent Prog. Horm. Res.* 53:119 (1998)), and tyrosyl phosphatase SHP2/Syp (Sun et al., *Mol. Cell. Biol.* 13:7418 (1993)). These binding events are critical to the activation of specific signaling pathways such as the Ras/Raf/MAPKK/MAPK cascade. Another major pathway of interest involves the binding of the p85 subunit of PI3K to the 613YMPM and 942YMKM motifs of IRS-1 (Backer et al., *EMBO J.* 11:3469 (1992); Myers et al., *Proc. Natl. Acad. Sci. USA* 89:10350 (1992)) which promotes cell survival by activating Akt/protein kinase B (PKB) (Dudek et al., *Science* 275:661 (1997); Eves et al., *Mol. Cell. Biol.* 18:2143 (1998)). PLCγ, acting on membrane phospholipids, produces second messengers, inositol phosphates and diacylglycerol, involved in control of intracellular $Ca^{2+}$ levels, and protein kinase C activity (Carpenter et al., *Exp. Cell Res.* 253:15 (1999); Sekiya et al., *Chem. Phys. Lipids* 98:3 (1999)). The N-terminal sequences of IRS-1 contain three important functional domains that mediate signaling: one has been identified as a pleckstrin homology (PH) region (Musacchio et al., *Trends Biochem. Sci.* 18:343 (1993)), and two others as phosphotyrosine binding (PTB) domains (Sun et al., *Nature* 377:173 (1995); Gustafson et al., *Mol. Cell. Biol.* 15:2500 (1995)). The PH domain mediates IRS-1 interactions with the Tyk-2 Janus tyrosine kinase (Platanias et al., *J. Biol. Chem.* 271:278 (1996)) and may mediate cross-talk between IRS-1 and G protein (Touhara et al., *J. Biol Chem.* 269:10217 (1994)) or phospholipids (Harlan et al., *Nature* 371:168 (1994)) signaling.

One of the most important downstream signaling molecules engaged by IRS proteins is PI3K, which phosphorylates phosphoinositides at the D-3 position (Carpenter et al., *Mol. Cell. Biol.* 13:1657 (1993); Dhand et al., *EMBO J.* 13:511 (1994)). These phospholipids activate phosphoinositide-dependent kinase-1 (PDK-1), which phosphorylates Akt, a serine kinase (also referred to as PKB) (Kandel et al., *Exp. Cell Res.* 253:210 (1999); Franke et al., *Cell* 81:727 (1995); Burgering et al., *Nature* 376:599 (1995)) and activates Akt kinase. Many trophic factors, including insulin, utilize the PI3K→PDK1 pathway to increase Akt activity. Lipid products of PI3K can also activate phosphoinositide-dependent kinases, small G-proteins and protein kinase C (Avruch et al., *Mol. Cell. Biochem.* 182:31 (1998); Le Good et al., *Science* 281:2042 (1998); Zheng et al., *J. Biol. Chem.* 269:18727 (1994)) signal transduction molecules. In addition, recent evidence suggests that PI3K can directly control the activities of individual components of the Ras/Raf/MAPK pathway (Chaudhary et al., *Curr. Biol.* 10:551 (2000)).

Several downstream targets of PI3K, such as Akt, play a critical role in regulating transcription and cell fate. These effects require delicate and accurate balancing signals necessary for survival and programmed cell death (apoptosis) (Burgering et al., *Nature* 376:599 (1995); Franke et al., *Cell* 88:435 (1997)). Insulin induces Akt phosphorylation on two sites (Thr308 and Ser473), thereby activating Akt kinase in a PI3K-dependent manner (Carpenter et al., *Mol. Cell. Biol.* 13:1657 (1993)). GSK3β, a ubiquitously expressed serine/threonine protein kinase, is another key element of the PI3K/Akt pathway (Kandel et al., *Exp. Cell Res.* 253:210 (1999); Avruch et al., *Mol. Cell. Biochem.* 182:31 (1998)). High levels of GSK3β activity promote apoptosis. Akt kinase promotes survival and inhibits apoptosis in part by phosphorylating GSK3 at Ser 9/21 (Pap et al., *J. Biol. Chem.* 273:19929 (1998)), which deactivates the kinase and inhibits GSK3β activity (Srivastava et al., *Mol. Cell. Biochem.* 182:135 (1998); Cross et al., *Nature* 378:785 (1995)). Biologic activity of GSK3β is of particular interest because this kinase may regulate the level and function of aspartyl (asparaginyl) β-hydroxylase (AAH), which is an insulin-regulated, ethanol-sensitive gene that is a downstream target of IRS-1 signaling and an important mediator of cell migration.

Akt-dependent phosphorylation of the pro-apoptotic protein BAD, a member of the Bcl-2 family, is another key event in the cell survival process. BAD and phospho-BAD levels participate in regulating the balance between apoptosis and insulin-induced cell survival. The BAD Ser112 site-specific kinase is a mitochondrial membrane-localized cAMP-dependent protein kinase (PKA) (Harada et al., *Mol. Cell* 3:413 (1999)), that promotes a subcellular kinase-substrate interaction whereby an outer mitochondrial membrane protein, A-kinase anchoring protein, tethers the PKA holoenzyme to the organelle where BAD is active. Upon exposure to a survival factor such as insulin, the localized catalytic subunit of PKA phosphorylates mitochondrial-based BAD on Ser112. Phosphorylation of BAD at Ser112 and Ser136 inactivates and displaces BAD from binding to Bcl-2, causing BAD to translocate to the cytosol. This process inhibits apoptosis and promotes cell survival (Zha et al., *Cell* 87:619 (1996)).

There is now compelling evidence that under some circumstances, Akt activity can inhibit apoptosis by regulating transcription factors that control the expression of cell death genes. Recently, it was demonstrated that Akt regulates the FKHRL1 gene, a member of the Forkhead family of transcription factors. When Akt is activated by insulin/IGF-I stimulation, presumably via the IRS-1 signal transduction pathway, it phosphorylates FKHRL1 and promotes its association with 14-3-3 chaperone proteins, resulting in retention of FKHRL1 transcription factor in the cytoplasm. In contrast, reduced phosphorylation of FKHRL1 by Akt can lead to its nuclear translocation and subsequent activation of target genes. In this regard, one of the most important targets of FKHRL1 is the Fas ligand (L) gene, which contains 3 consensus sequences for FKHRL1 DNA binding. Binding of FKHRL1 to the Fas L promoter region increases Fas L gene expression and promotes cell death (Brunet et al., *Curr. Opin. Neurobiol.* 11:297 (2001)). Thus, inhibition of Akt signaling induces Fas L expression (Suhara et al., *Mol. Cell. Biol.* 22:680 (2002)). In this regard, the findings in previous experiments suggest that acute or chronic ethanol consumption may lead to up-regulated Fas L expression in rats and mice (Deaciuc et al., *Alcohol Clin. Exp. Res.* 23:349 (1999); Zhou et al., *Am. J. Pathol.* 159:329 (2001); Deaciuc et al., *Hepatol. Res.* 19:306 (2001); Castaneda et al., *J. Cancer Res. Clin. Oncol.* 127:418 (2001)), although the mechanism(s) has not yet been determined. It has been suggested that Fas L gene upregulation in the setting of chronic ethanol abuse may occur via reduced Akt dependent phosphorylation of Forkhead transcription factors, and this process activates programmed cell death mechanisms in hepatocytes. Therefore, it is important to recognize the biologic consequences of ethanol-induced alterations in both IRS-1-dependent and IRS-1-independent signaling mechanisms as they pertain to hepatocyte proliferation and survival.

There is direct experimental evidence that ethanol reduces PI3K activity in the liver by an IRS-1 dependent pathway. However, consideration of other potential mechanisms by which PI3K might be inhibited by ethanol led to examination of PTEN expression in the liver. The rationale for these experiments is that PTEN has emerged as a key negative regulator of PI3K activity (Yamada et al., *J. Cell Sci.* 114:2375 (2001); Seminario et al., *Semin. Immunol.* 14:27 (2002); Leslie et al., *Cell Signal.* 14:285 (2002); Maehama et al., *Annu. Rev. Biochem.* 70:247 (2001); Comer et al., *Cell* 109:541 (2002)). The PTEN molecule has multiple conserved domains such as a C2 phospholipid binding domain, two PEST regions, a PDZ binding domain, and a PIP2 binding motif. Initially described as a tumor suppressor gene, it has now been determined that the major substrates (in vivo) are PI (3, 4, 5) $P_3$ and PI (4, 5) $P_2$. The presence of a point mutation that abrogates only the lipid phosphatase domain of PTEN (G-129-E) is sufficient to produce a PTEN –/– phenotype including loss of tumor suppression. On the other hand, overexpression of PTEN blocks IRS-1 tyrosyl phosphorylation and IRS-1/Grb-2/SOS complex formation without interfering with tyrosyl phosphorylation of the insulin receptor. The net effect within the cell is to inhibit MAPK activation, cell cycle progression, and proliferation (Weng et al., *Hum. Mol. Genet.* 10:605 (2001)). These findings suggest that PTEN negatively regulates signaling pathways involved in hepatocyte proliferation.

Thus, it is of great interest with respect to ethanol effects on the liver that PTEN dephosphorylates and inhibits PI3K function (Dahia et al., *Hum. Mol. Genet.* 8:185 (1999); Maehama et al., *Trends Cell. Biol.* 9:125 (1999); Li et al., *Cancer Res.* 57:2124 (1997)). Conversely, inactivation of PTEN enhances PI3K function and promotes membrane recruitment of Akt leading to increased Akt phosphorylation and Akt kinase activity (Kandel et al., *Exp. Cell Res.* 253:210 (1999); Maehama et al., *Trends Cell. Biol.* 9:125 (1999)). Therefore, low levels of PTEN increase Akt kinase activity and promote growth and survival, whereas high levels of PTEN inhibit PI3K/Akt and enhance transmission of apoptotic signals, as well as inhibit cell proliferation. There is significantly increased PTEN expression and phosphatase activity in liver tissue derived from chronic ethanol-exposed rats relative to control rats. This phenomenon may be due to transcriptional, post-translational or both mechanisms. In this regard, PTEN expression and phosphatase activity are negatively regulated by phosphorylation (Torres et al., *J. Biol. Chem.* 276:993 (2001)), and suggest that PTEN levels may be controlled by insulin-induced phosphorylation in primary hepatocyte cultures, and that ethanol exposure enhances the biologic activity and levels of the protein by altering phosphorylation of the C-terminal region of the molecule. It is noteworthy that in ethanol-exposed liver tissue the magnitude of increased PTEN expression was paralleled by enhanced GSK-3β activity, consistent with the expected inhibitory effects of PTEN on downstream signaling through PI3K. This observation suggests that ethanol may have a major effect in the liver on both programmed cell death as well as proliferative pathways through modulation of PTEN expression.

The biologic significance as it applies to human disease is that ethanol may adversely affect specific signaling cascades related to both hepatocyte proliferation and survival as regulated by insulin and insulin like growth factors (IGF-I and IGF-II) and IRS-1-dependent and IRS-1-independent signal transduction cascades. There are ethanol effects on the Fas system, which appears to be linked to impaired PI3K/Akt signaling. Proliferative and survival pathways through IRS-1 and PI3K are strikingly altered by chronic ethanol exposure in vivo, and the Fas signaling pathway may contribute to hepatocyte apoptosis both in vitro and in vivo. Indeed, there is accumulating evidence that ethanol upregulates Fas L expression, and may play an important role in hepatocyte injury observed in alcoholics with liver disease, but the molecular mechanism(s) of Fas Receptor (R)/Fas L alterations by ethanol remain to be established (Benedetti et al., *J. Hepatol.* 6:137 (1988); Natori et al., *J. Hepatol.* 34:248 (2001); Goldin et al., *J. Pathol.* 171:73 (1993); Nanji, *Semin. Liver Dis.* 18:187 (1998); Higuchi et al., *Hepatology* 34:320 (2001)).

Another adverse effect of chronic ethanol consumption on the liver relates to oxidative stress as manifested by lipid peroxidation and DNA damage. In this regard, ethanol exposure to the liver increases cellular production of reactive oxygen species (ROS) that includes $H_2O_2$. When this occurs, the anti-oxidant defenses are inadequate, hepatocyte viability decreases and liver damage is produced (Sohn et al., *J. Neurol. Sci.* 162:133 (1999); Tanaka et al., *J. Clin. Invest.* 103:341 (1999); Diehl et al., *Am. J. Physiol. Gastrointest. Liver Physiol.* 288:1 (2005)). In this setting, there is increased liver inflammation that leads to chronic disease such as fatty liver, alcoholic hepatitis, cirrhosis and in some cases the development of hepatocellular carcinoma. Therefore chronic ethanol consumption has two major adverse effects on the liver, namely the induction and perpetuation of liver injury through oxidative stress, mitochondrial damage, upregulation of programmed cell death pathways, DNA damage and inhibition of the hepatic repair process (i.e. liver regeneration) principally through the insulin/IGF-I signal transduction cascades and it is one of the major causes of human liver disease throughout the world.

The magnitude of this problem is illustrated by the following: approximately 67% of adults consume alcohol and 14 million Americans meet the criteria for alcohol abuse and/or dependence. In this context, alcoholic liver disease (ALD) affects more than 2 million Americans and many more worldwide. The clinical consequences are that 40% of individuals with ALD die from cirrhosis of the liver. Thus, there is a real need to discover ways to prevent or treat these dreaded complications of ethanol abuse.

SUMMARY OF THE INVENTION

A relationship between alcohol-induced liver damage and insulin resistance has been demonstrated by the finding of impaired insulin response and alterations in the insulin/IGF pathways in the liver of animals with chronic alcohol intake. These findings define a connection between ALD and the insulin/IGF signaling pathway that may be exploited for therapeutic purposes.

This invention relates to the surprising discovery that administration of certain peroxisome proliferator activated receptor (PPAR) agonists strikingly inhibit oxidative stress and DNA damage in the liver using an animal model of ALD and, more important, dramatically enhances liver regeneration. The net effect is to attenuate or prevent ongoing liver injury produced by ethanol and to greatly accelerate the hepatic repair process. This invention has major implications for the treatment of liver damage and ALD.

Thus, one aspect of the present invention is directed to methods for treating, preventing, or reversing alcohol-induced liver disease in an animal, comprising administering to said animal a therapeutically effective amount of at least one PPAR agonist.

Another aspect of the invention is directed to methods for treating, preventing, or reversing liver damage produced by chronic alcohol intake in an animal, comprising administering to said animal a therapeutically effective amount of at least one PPAR agonist.

In one embodiment, the invention relates to methods for treating, preventing, or reversing insulin resistance in the liver of an animal produced by chronic alcohol intake, comprising administering to said animal a therapeutically effective amount of at least one PPAR agonist.

In a further embodiment, the invention relates to methods for stimulating or restoring hepatic regenerative response in an animal with chronic alcohol intake, comprising administering to said animal a therapeutically effective amount of at least one PPAR agonist.

Surprisingly, it has been discovered that PPAR agonists are particularly effective for treatment and prevention of liver damage in chronic ethanol-fed animals, a model of ALD. Further, the PPAR agonists rescue ethanol-impaired hepatic regeneration in this model. Thus, it is expected that human subjects who are chronic alcohol drinkers or who suffer from alcohol-induced liver damage or liver disease may be administered PPAR agonists to prevent or slow down further liver damage, to promote the generation of healthy liver tissue and to treat or ameliorate the symptoms of liver damage or liver disease.

The invention further provides an animal model of alcohol-induced liver damage and disease produced by chronically feeding ethanol to Long-Evans rats. Surprisingly, it has been discovered that Long-Evans rats exhibit a robust response to ethanol feeding compared to other rat strains that make the rats ideally suited for the study of the effects of chronic alcohol intake. In one embodiment, ethanol is included in the daily diet of Long-Evans rats. For example, ethanol may comprise about 0%, 2%, 4.5%, 6.5%, 9.25% (v/v) (equivalent to 0%, 8%, 18%, 26%, or 37% of the caloric content) or more of the daily diet.

The invention further relates to a method for screening for an agent that is potentially useful for the treatment, prevention or reversal of alcohol-induced liver damage or disease, comprising administering an agent to the animal model produced by chronically feeding ethanol to Long-Evans rats and determining the level of liver damage, insulin resistance, and/or hepatic regeneration response relative to the level in a control animal that has not had the agent administered, wherein an improvement in the level of liver damage, insulin resistance, and/or hepatic regeneration response relative to the level in a control animal that has not had the agent administered indicates that the agent is potentially useful for the treatment, prevention or reversal of alcohol-induced liver damage or disease.

The invention additionally provides a method for testing a potential treatment for treatment, prevention or reversal of alcohol-induced liver damage or disease, comprising administering the potential treatment to the animal model produced by chronically feeding ethanol to Long-Evans rats and determining the level of liver damage, insulin resistance, and/or hepatic regeneration response relative to the level in a control animal that has not had the potential treatment administered, wherein an improvement in the level of liver damage, insulin resistance relative, and/or hepatic regeneration response to the level in a control animal that has not had the potential treatment administered indicates that the treatment is potentially useful for the treatment, prevention or reversal of alcohol-induced liver damage or disease.

BRIEF DESCRIPTION OF THE DRAWINGS/FIGURES

FIG. 1 demonstrates liver damage (top), enhanced lipid peroxidation (middle), and DNA damage (bottom) by chronic ethanol feeding compared to isocaloric pair fed controls.

FIGS. 2A-2F show the measurement of insulin, IGF-I, and IGF-II gene expression in ethanol and control animals (A, B, and C) compared to their respective receptor expression (D, E, and F) by real time RT-PCR.

FIGS. 3A-3C demonstrate reduced insulin binding to its receptor in chronic ethanol fed rats (A). Note there are no changes in IGF-I or IGF-II receptor binding as compared to controls (B, C).

FIGS. 4A-4C show that there are no differences in IRS-1, 2 and 4 gene expression between ethanol fed animals and controls (A-C). Note the decrease in AAH expression which is an insulin responsive gene in the chronic ethanol fed group (D). This result demonstrates insulin resistance in the liver.

FIG. 5 shows that chronic ethanol feeding impairs liver regeneration as measured by BrdU incorporation at 24 hours after partial hepatectomy.

FIG. 6 shows that PPAR agonists rescue ethanol-induced inhibition of liver regeneration. Note that PPAR-δ agonist treatment returns the liver regenerative response to normal levels as measured by BrdU incorporation. PPAR-δ and PPAR-α agonists have more modest beneficial effects on liver repair.

FIGS. 9A-9L show the effects of PPAR agonists on liver architecture in control animals.

FIGS. 10A-10L show the effects of PPAR agonists on liver architecture in ethanol-fed animals.

FIG. 16A-16D show the effects of ethanol and PPAR agonist treatments on AAH and GAPDH expression by Western analysis.

DETAILED DESCRIPTION OF THE INVENTION

Figure 1:
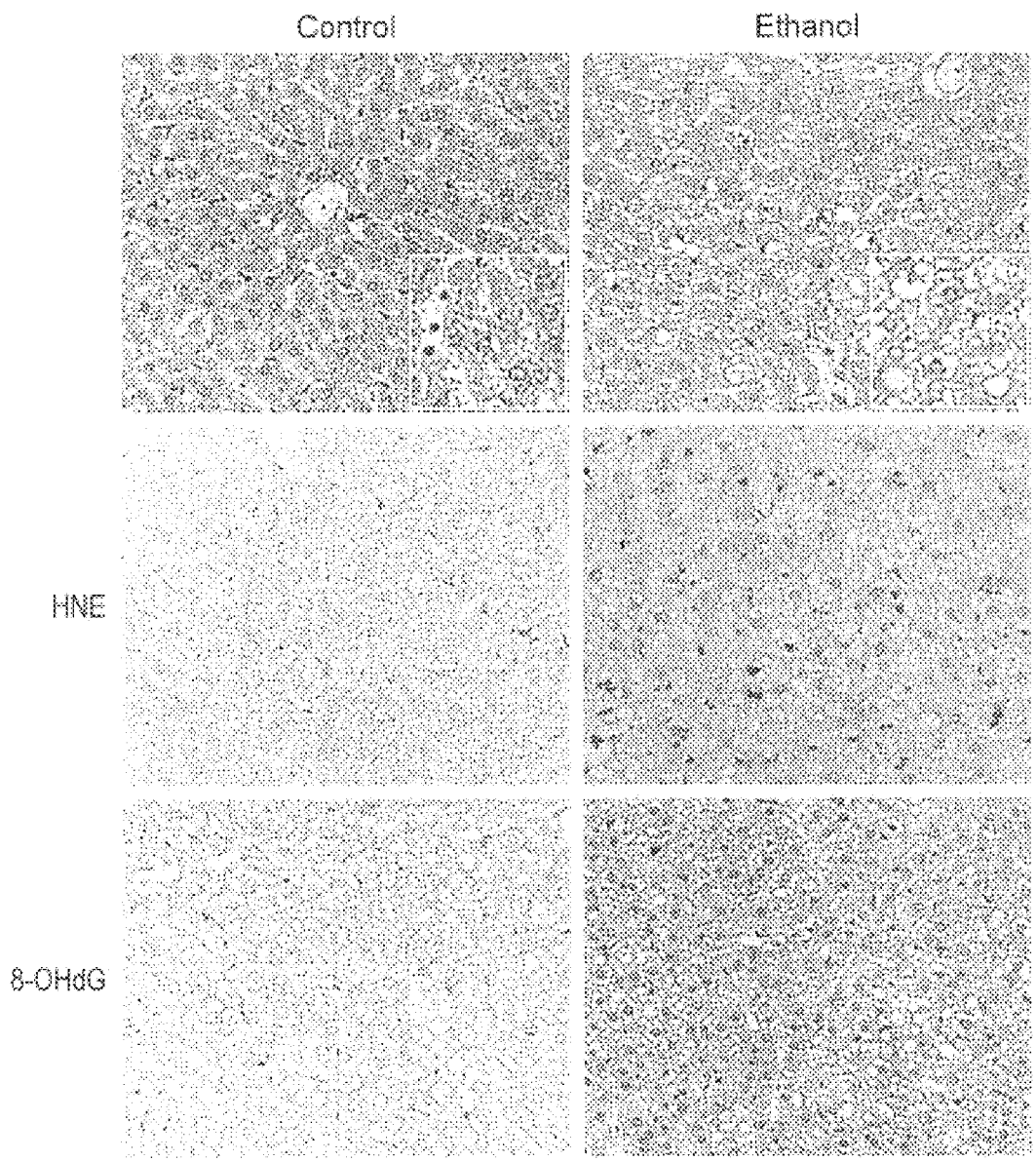

The present invention relates to the important role played by increased insulin resistance in the occurrence of alcohol-induced liver damage and disease and the ability of PPAR agonists to prevent or treat the liver damage and restore hepatic regeneration response. Administration of PPAR agonists to animals that chronically ingest alcohol blocks the liver damage that occurs in response to the alcohol intake, including damage due to oxidative stress (e.g., lipid peroxidation) and DNA damage. Further, the administration of PPAR agonists reverses the inhibition of hepatic regeneration response that occurs during chronic alcohol intake.

Therefore, the invention relates to methods for treating, preventing, or reversing alcohol-induced liver disease in an animal, comprising administering to said animal a therapeutically effective amount of at least one PPAR agonist.

Another aspect of the invention is directed to methods for treating, preventing, or reversing liver damage produced by chronic alcohol intake in an animal, comprising administering to said animal a therapeutically effective amount of at least one PPAR agonist.

In one embodiment, the invention relates to methods for treating, preventing, or reversing insulin resistance in the liver of an animal produced by chronic alcohol intake, comprising administering to said animal a therapeutically effective amount of at least one PPAR agonist.

In a further embodiment, the invention relates to methods for stimulating or restoring hepatic regenerative response in an animal with chronic alcohol intake, comprising administering to said animal a therapeutically effective amount of at least one PPAR agonist.

In one embodiment of the invention, at least two different PPAR agonists are administered. In another embodiment, at least three different PPAR agonists are administered. In one embodiment, the PPAR agonists that are administered bind to at least two different subtypes of PPAR receptors, e.g., α and δ, α and γ, or δ and γ. In a further embodiment, the PPAR agonists that are administered bind to all three subtypes of PPAR receptors. The PPAR agonists administered may include compounds that selectively bind to one PPAR receptor subtype and/or compounds that bind to more than PPAR receptor subtype.

The term "Alcoholic Liver Disease (ALD)," as used herein, refers to the spectrum of clinical pathologic changes in the liver caused by ethanol intake. ALD pathologies include fatty liver (steatosis), alcoholic hepatitis, and alcoholic cirrhosis.

The term "chronic alcohol intake," as used herein, refers to the consumption by an animal of at least about 0.1 g pure alcohol (ethanol) per kg body weight per day on average, e.g., at least about 0.2, 0.3, 0.4, 0.5, 1, 2, 3, 4, or 5 g/kg/day on average. For a human, chronic alcohol intake is considered to be at least about 10 g pure alcohol per day on average, e.g., at least about 20, 30, 40, 50, 60, 70, 80, 90, or 100 g/day on average.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of liver disease, in one embodiment, a therapeutically effective amount will refer to the amount of a therapeutic agent that decreases the number of damaged hepatocytes, slows the rate of increase in the number of damaged hepatocytes, increases the rate of liver regeneration, or increases survival time by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In a further embodiment, a therapeutically effective amount will refer to the amount of a therapeutic agent that increases a biological function of the liver by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. Liver function can be measured using assays that are routine in clinical medicine, including without limitation measurement of transaminases (e.g., alanine aminotransferase (ALT), aspartate aminotransferase (AST)), γ-glutamyl transpeptidase (GGT), mean corpuscular volume (MCV), prothrombin time, platelet count, bilirubin, albumin, and/or alkaline phosphatase. In an additional embodiment, a therapeutically effective amount will refer to the amount of a therapeutic agent that decreases insulin resistance in the liver by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. Insulin resistance can be measured using assays that are routine in the art and those that are discussed herein, including without limitation measurement of insulin binding to the insulin receptor, glucose tolerance tests, and expression of insulin-responsive genes.

The terms "prevent," "preventing," and "prevention," as used herein, refer to a decrease in the occurrence of pathological cells (e.g., damaged hepatocytes) in an animal. The prevention may be complete, e.g. the total absence of pathological cells in a subject. The prevention may also be partial, such that the occurrence of pathological cells in a subject is less than that which would have occurred without the present invention.

In one aspect of the invention, methods for treating, preventing, or reversing alcohol-induced liver disease in an animal are provided. In certain embodiments, the methods comprise the administration to the animal of a therapeutically effective amount of at least one PPAR agonist. The PPAR agonist may be administered prior to or after the onset of physical or histological symptoms of liver disease. In one embodiment, the liver disease is steatosis, alcoholic hepatitis, or alcoholic cirrhosis.

Another aspect of the invention is directed to methods for treating, preventing, or reversing liver damage produced by chronic alcohol intake in an animal. In certain embodiments, the methods comprise the administration to the animal of a therapeutically effective amount of at least one PPAR agonist. The PPAR agonist may be administered prior to or after the onset of physical or histological symptoms of liver damage. Liver damage may be any type of cellular or tissue damage associated with alcohol intake. For example, the damage may be associated with oxidative stress (e.g., lipid peroxidation) or DNA damage. The term "associated with," as used herein, means that the alcohol-induced liver damage is evidenced by physical (e.g., histological, serological) signs of a condition (e.g., oxidative stress or DNA damage).

In one embodiment, the invention relates to methods for treating, preventing, or reversing insulin resistance in the liver of an animal produced by chronic alcohol intake. In certain embodiments, the methods comprise the administration to the animal of a therapeutically effective amount of at least one PPAR agonist. The PPAR agonist may be administered prior to or after the onset of insulin resistance. Insulin resistance may be due to alcohol-induced alterations anywhere along the insulin/IGF signaling pathways, e.g., decreased binding of insulin to the insulin receptor, decreased IGF-I expression, increased IGF-II expression, increased expression of receptors for IGF-I and IGF-II, or decreased expression of insulin-responsive genes such as AAH.

Insulin resistance may be measured by detecting an alteration in the level or function of at least one factor in the insulin/IGF signaling pathway. In one embodiment, the detection of an alteration is carried out in vivo. For example, imaging techniques (e.g., magnetic resonance imaging, computed axial tomography, single photon emission computed tomography, positron emission tomography, X-ray, ultrasound) may be used in combination with detectably labeled antibodies, ligands, enzymes substrates, etc., to determine the level or function of at least one factor in the insulin/IGF signaling pathway in a subject. Examples of detectable labels include, but are not limited to, radioactive, fluorescent, paramagnetic, and superparamagnetic labels. Any suitable in vivo imaging techniques known in the art may be used in the present invention. Examples of imaging techniques are disclosed in U.S. Pat. Nos. 6,737,247, 6,676,926, 6,083,486, 5,989,520, 5,958,371, 5,780,010, 5,690,907, 5,620,675, 5,525,338, 5,482,698, and 5,223,242.

In another embodiment, the detection of an alteration is carried out in vitro, e.g., using a biological sample. A biological sample may be any tissue or fluid from a subject that is suitable for detecting the level or function of at least one factor in the insulin/IGF signaling pathway. Examples of useful samples include, but are not limited to, biopsied hepatic tissues, blood, plasma, serous fluid, cerebrospinal fluid, saliva, urine, and lymph.

Factors in the insulin/IGF signaling pathway that may be detected and measured include, but are not limited to, insulin, insulin-like growth factor-I (IGF-I), IGF-II, insulin receptor, IGF-I receptor, IGF-II receptor, tyrosine phosphorylated insulin receptor, tyrosine phosphorylated IGF-I receptor, tyrosine phosphorylated IGF-II receptor, insulin receptor substrate-1 (IRS-1), IRS-2, IRS-4, tyrosine phosphorylated IRS-1, tyrosine phosphorylated IRS-2, tyrosine phosphorylated IRS-4, phosphatidylinositol 3-kinase (PI3 kinase), the p85 subunit of PI3 kinase, Akt, phospho-Akt, glycogen synthase kinase-3β (GSK-3β), and phospho-GSK-3β. Functions that may be measured include, but are not limited to, ligand binding capacity of the insulin receptor, IGF-I receptor, or IGF-II receptor, kinase activity of the insulin receptor, IGF-I receptor, or IGF-II receptor, interaction of the p85 subunit of PI3 kinase with phosphorylated IRS-1, IRS-2, or IRS-4, binding of phosphorylated IRS-1, IRS-2, or IRS-4 to growth factor receptor-bound protein 2 (Grb2), SHPTP-2 protein tyrosine phosphatase, or the p85 subunit of PI3 kinase, the enzymatic activity of mitogen-activated protein kinase kinase (MAPKK), Erk MAPK, Akt/Protein kinase B, GSK-3β.

The levels of factors in the insulin/IGF signaling pathway may be measured at the protein or RNA (e.g., mRNA) levels. Any method known in the art for quantitating specific proteins in a biological sample may be used in the present methods. Examples include, but are not limited to, immunoassays, Western blotting, immunoprecipitation, inmmuno-histochemistry, gel electrophoresis, capillary electrophoresis, column chromatography, ligand binding assays, and enzymatic assays. See, e.g., Harlow et al., Antibodies: A Laboratory Manual, Cold Spring Harbor Laboratory, Cold Spring Harbor, N.Y., (1988); Ausubel et al., Current Protocols in Molecular Biology, John Wiley & Sons, New York 3rd Edition, (1995).

To measure the level of a specific RNA, any assay known in the art for the detection of nucleic acids may be used in the invention. Examples include, but are not limited to, reverse transcription and amplification assays, hybridization assays, Northern blotting, dot blotting, in situ hybridization, gel electrophoresis, capillary electrophoresis, and column chromatography. See, e.g., Ausubel et al., Current Protocols in Molecular Biology, John Wiley & Sons, New York 3rd ed., (1995); Sambrook et al., Molecular Cloning—A Laboratory Manual, 2nd ed., Vol. 1-3 (1989). The assay can detect the RNA itself or a cDNA produced by reverse transcription of the RNA. Assays can be performed directly on biological samples or on nucleic acids isolated from the samples.

In a further embodiment, the invention relates to methods for stimulating or restoring hepatic regenerative response in an animal. In certain embodiments, the methods comprise the administration to the animal of a therapeutically effective amount of at least one PPAR agonist. The PPAR agonist may be administered prior to or after the reduction in hepatic regenerative response. The increase in regenerative response induced by a PPAR agonist may be at least about 10% greater than the regenerative response seen in the absence of the PPAR agonist, e.g., at least about 20%, 30%, 40%, 50%, 60%, 70%, 80%, 90%, or 100% greater. Measurement of hepatic regenerative response may be carried out by any technique known in the art, such as measurement of DNA synthesis rates.

The methods of the invention may be carried out on animals displaying pathology resulting from liver damage or disease, animals suspected of displaying pathology resulting from liver damage or disease, and animals at risk of displaying pathology resulting from liver damage or disease. For example, those that have a genetic predisposition to alcoholism or who are moderate drinkers but already have liver damage for other reasons (e.g., viral hepatitis) can be treated prophylactically.

PPAR agonists that may be used in the present invention include selective agonists of PPAR-α, PPAR-γ, and PPAR-δ, as disclosed in U.S. Pat. Nos. 6,713,514, 6,677,298, 6,462,046, 5,925,657, and 5,326,770 and in Combs et al., *J. Neurosci.* 20:558 (2000), as well as compounds that are agonists of multiple PPAR subtypes. The term selective is used to describe agents having greater than 10-fold, preferably greater than 100-fold, and most preferably greater than 1,000-fold activity at one PPAR receptor subtype than at another PPAR receptor subtype. Characterization of receptor affinities and functional activities for agents at PPAR receptor subtypes can be determined using methodology as described in WO 2005049572. The use of PPAR-δ agonists in liver disease patients may have an added advantage of increasing the number of type I muscle fibers, which may confer resistance to obesity and improve metabolic profiles, even in the absence of exercise (Wang et al., *PLoS Biol.* 2:3294 (2004)).

Useful PPAR-α selective agonists include without limitation clofibrate, bezafibrate, ciprofibrate, 2-bromohexadecanoic acid, etomoxir sodium hydrate, N-oleoylethanolamine, GW-9578, GW-7647, WY-14643, and compounds disclosed in U.S. Pat. Nos. 7,091,225, 7,091,230, 7,049,342, 6,987,118, 6,750,236, 6,699,904, 6,548,538, 6,506,797, 6,306,854, 6,060,515, and 6,028,109.

Useful PPAR-γ selective agonists include without limitation ciglitazone, rosiglitazone, pioglitazone, troglitazone, GW-1929, F-L-Leu, JTT-501, GI-262570, and compounds disclosed in U.S. Pat. Nos. 7,090,874, 7,060,530, 6,908,908, 6,897,235, 6,852,738, 6,787,651, 6,787,556, 6,713,514, 6,673,823, 6,646,008, 6,605,627, 6,599,899, 6,579,893, 6,555,536, 6,541,492, 6,525,083, 6,462,046, 6,413,994, 6,376,512, 6,294,580, 6,294,559, 6,242,196, 6,214,850, 6,207,690, 6,200,995, 6,022,897, 5,994,554, 5,939,442, and 5,902,726.

Useful PPAR-δ selective agonists include without limitation GW-501516, GW-0742, L-165041, and carbaprostacyclin, which are structurally defined below:

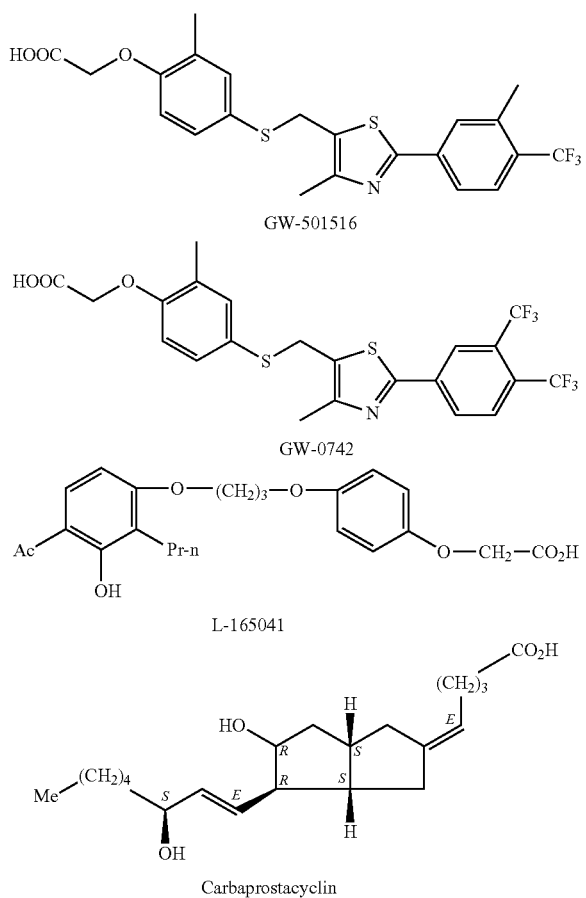

GW-501516

GW-0742

L-165041

Carbaprostacyclin

Other useful PPAR-δ agonists include without limitation RWJ-800025, L-160043 and compounds disclosed in U.S. Pat. Nos. 7,091,245, 7,015,329, 6,869,967, 6,787,552, 6,723,740, 6,710,053, and 6,300,364 and in EP 1586573, US 20050245589, and WO 2005049572.

Useful mixed PPAR-α/γ agonists include without limitation GW-1556, AVE-8042, AVE-8134, AVE-0847, DRF-2519, and compounds disclosed in U.S. Pat. Nos. 7,091,230, 6,949,259, 6,713,508, 6,645,997, 6,569,879, 6,468,996, 6,465,497, and 6,380,191.

Useful compounds that act as agonists at all PPAR receptors include without limitation LY-171883 and pseudolaric acid B.

Some embodiments of the present invention provide methods for administering a therapeutically effective amount of a PPAR agonist in combination with an additional agent known in the art to be useful for the treatment, prevention, or reversal of alcohol-induced liver disease or damage. Examples of additional agents include without limitation glucocorticoids (e.g., prednisone, prednisolone), pentoxifylline, ursodeoxycholic acid, colchicine, and diuretics (e.g., amiloride, furosemide).

In some embodiments of the invention, a PPAR agonist and an additional agent are administered to an animal separately, e.g. as two separate compositions. In other embodiments a PPAR agonist and an additional agent are administered as a part of a single composition.

In some embodiments of the present invention, a PPAR agonist and an additional agent are administered to an animal under one or more of the following conditions: at different periodicities, at different durations, at different concentrations, by different administration routes, etc. In some embodiments, a PPAR agonist is administered prior to an additional agent, e.g., 0.5, 1, 2, 3, 4, 5, 10, 12, or 18 hours, 1, 2, 3, 4, 5, or 6 days, or 1, 2, 3, or 4 weeks prior to the administration of an additional agent. In some embodiments, a PPAR agonist is administered after an additional agent, e.g., 0.5, 1, 2, 3, 4, 5, 10, 12, or 18 hours, 1, 2, 3, 4, 5, or 6 days, or 1, 2, 3, or 4 weeks after the administration of an additional agent. In some embodiments, a PPAR agonist and an additional agent are administered concurrently but on different schedules, e.g., a PPAR agonist is administered daily while an additional agent is administered once a week, once every two weeks, once every three weeks, or once every four weeks. In other embodiments, a PPAR agonist is administered once a week while an additional agent is administered daily, once a week, once every two weeks, once every three weeks, or once every four weeks.

The administration of a PPAR agonist may be continued concurrently with the administration of an additional agent. Additionally, the administration of a PPAR agonist may be continued beyond the administration of an additional agent or vice versa.

In certain embodiments of the invention, the method of administering a PPAR agonist in combination with an additional agent may be repeated at least once. The method may be repeated as many times as necessary to achieve or maintain a therapeutic response, e.g., from one to about 10 times or more. With each repetition of the method the PPAR agonist and the additional agent may be the same or different from that used in the previous repetition. Additionally, the time period of administration of the PPAR agonist and the additional agent and the manner in which they are administered can vary from repetition to repetition.

The agents of the present invention may be linked to a carrier molecule to enhance the cellular uptake of the compounds. Examples of such carrier molecules include carrier peptides such as those described by Fulda et al., Nature Med. 8:808 (2002), Arnt et al., J. Biol. Chem. 277:44236 (2002), and Yang et al., Cancer Res. 63:831 (2003), fusogenic peptides (see, e.g., U.S. Pat. No. 5,965,404), and viruses and parts of viruses such as empty capsids and virus hemagglutinin (see, e.g., U.S. Pat. No. 5,547,932). Other carrier molecules include ligands for cell surface receptor such as asialoglycoprotein (which binds to the asialoglycoprotein receptor; see U.S. Pat. No. 5,166,320) and antibodies to cell surface receptors such as antibodies specific for T-cells, e.g., anti-CD4 antibodies (see U.S. Pat. No. 5,693,509).

Compositions within the scope of this invention include all compositions wherein the agents of the present invention are contained in an amount which is effective to achieve its intended purpose. While individual needs vary, determination of optimal ranges of effective amounts of each component is within the skill of the art. The actual dosage and treatment regimen can be readily determined by the ordinary skilled physician, taking into account the route of administration, age, weight, and health of the subject, as well as the stage of liver disease, and, of course, any side effects of the agents, efficacy of the agents, and in accordance with customary medical procedures and practices. Typically, the agents may be administered to animals, e.g. humans, orally at a dose of 0.0025 to 50 mg/kg, or an equivalent amount of the pharmaceutically acceptable salt thereof, per day of the body weight of the animal being treated for liver damage or disease. Preferably, about 0.01 to about 10 mg/kg is orally administered to treat, prevent, or reverse liver damage or disease. For intramuscular injection, the dose is generally about one-half of the oral dose. For example, a suitable intramuscular dose would be about 0.0025 to about 25 mg/kg, and most preferably, from about 0.01 to about 5 mg/kg.

The unit oral dose may comprise from about 0.01 to about 50 mg, preferably about 0.1 to about 10 mg of each agent. The unit dose may be administered one or more times daily as one or more tablets or capsules each containing from about 0.1 to about 10, conveniently about 0.25 to 50 mg of the agents.

In addition to administering agents as raw chemicals, the agents of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally or topically and which can be used for the preferred type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by injection, topically or orally, contain from about 0.01 to 99 percent, preferably from about 0.25 to 75 percent of active compound(s), together with the excipient.

The pharmaceutical compositions of the invention may be administered to any subject which may experience the beneficial effects of the compounds of the invention. Foremost among such subjects are mammals, e.g., humans, although the invention is not intended to be so limited. Other animals include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal, or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The invention further provides an animal model of alcohol-induced liver damage and disease produced by chronically feeding ethanol to Long-Evans rats. Surprisingly, it has been discovered that Long-Evans rats exhibit a robust response to ethanol feeding compared to other rat strains that make the rats ideally suited for the study of the effects of chronic alcohol intake. In one embodiment, ethanol is included in the daily diet of Long-Evans rats. For example, ethanol may comprise about 0%, 2%, 4.5%, 6.5%, 9.25% (v/v) (equivalent to 0%, 8%, 18%, 26%, or 37% of the caloric content) or more of the daily diet. In one embodiment, ethanol comprises about 37% of the caloric content of the daily diet. Ethanol feeding may continue for as long as desired, e.g., from as little as two days to as long as six months or more. In one embodiment, ethanol feeding is continued until liver damage and/or reduction in hepatic regeneration response is induced, e.g., for 1, 2, 3, 4, 5, or 6 weeks or more, followed by the administration of agents or other treatments to determine their effect on the liver damage or hepatic regeneration response. In another embodiment, agents or treatments are administered prior to or concurrently with ethanol feeding to determine if liver damage or the reduction in hepatic regeneration response can be prevented or slowed.

The invention further relates to a method for screening for an agent that is potentially useful for the treatment, prevention or reversal of alcohol-induced liver damage or disease, comprising administering an agent to the animal model produced by chronically feeding ethanol to Long-Evans rats and determining the level of liver damage, insulin resistance, and/or hepatic regeneration response relative to the level in a control animal that has not had the agent administered, wherein an improvement in the level of liver damage, insulin resistance, and/or hepatic regeneration response relative to the level in a control animal that has not had the agent administered indicates that the agent is potentially useful for the treatment, prevention or reversal of alcohol-induced liver damage or disease.

Agents that may be screened include proteins, polypeptides, peptides, antibodies, nucleic acids, organic molecules, natural products, chemical libraries, and the like.

The invention additionally provides a method for testing a potential treatment for treatment, prevention or reversal of alcohol-induced liver damage or disease, comprising administering the potential treatment to the animal model produced by chronically feeding ethanol to Long-Evans rats and determining the level of liver damage, insulin resistance, and/or hepatic regeneration response relative to the level in a control animal that has not had the potential treatment administered, wherein an improvement in the level of liver damage, insulin resistance, and/or hepatic regeneration response relative to the level in a control animal that has not had the potential treatment administered indicates that the treatment is potentially useful for the treatment, prevention or reversal of alcohol-induced liver damage or disease.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

Example 1

General Methods
Experimental Design

In these studies, Long-Evans male rats were fed a 37% ethanol liquid diet for 6 weeks. An isocaloric (sucrose substituted for ethanol) diet was administered to pair fed control animals. After three weeks, both groups of rats were injected with either PPAR-α, γ, or δ agonists or saline as a control. The PPAR-α (GW7647), PPAR-γ (F-L-Leu) and PPAR-δ (L-165,041) activators were obtained from CalBiochem (Carlsbad, Calif.) and administered intraperitoneal (IP) at concentrations of 25 µg/kg, 20 µg/kg and 2 µg/kg respectively. The mice were given IP injections twice a week. At 6 weeks, the animals underwent 2/3 partial hepatectomy. The removed liver was used for histology, measurement of lipid peroxidation, DNA damage and insulin/IGF signaling as described below. Following 2/3 hepatectomy, the liver remnants were harvested 18, 24, 30 and 48 hours later to assess the regenerative response. To do this, animals were injected IP with BrdU 2 hours before harvest to measure its incorporation into hepatic nuclei as an index of DNA synthesis. Liver regeneration as measured by BrdU or $^3$H-thymidine incorporation is maximal 24 hours after partial hepatectomy in this animal model (Wands et al., Gastroenterology 77:528 (1979)).

Liver tissue from chronic ethanol fed rats and isocaloric pair fed controls were obtained following sacrifice after 6 weeks on these diets. Formalin fixed paraffin-embedded sections of liver regions were stained with hematoxylin and eosin dyes and examined by light microscopy. Adjacent histological sections were subjected to immunohistochemical staining. Fresh, snap-frozen blocks of tissue from the same regions were used to measure mRNA expression and receptor binding.

Histological Studies:

Paraffin sections (8 µm thick) were immunostained with monoclonal antibodies to 8-hydroxy-deoxyguanosine (8-OHdG) (Oxis Research) or 4-hydroxynonenol (HNE) (Chemicon International, Temecula, Calif.), to detect DNA damage and lipid peroxidation, respectively. Prior to immunostaining, the deparaffinized, re-hydrated sections were treated with 0.1 mg/ml saponin in phosphate buffered saline (10 mM sodium phosphate, 0.9% NaCl, pH 7.4; PBS) for 20 minutes at room temperature, followed by 3% hydrogen peroxide in methanol for 10 minutes to quench endogenous peroxidase activity, and then a 30-minute incubation in SuperBlock-TBS (Pierce Chemical Co., Rockford, Ill.) to block non-specific binding sites. The tissue sections were then incubated overnight at 4° C. with 0.5-1 µg/ml of primary antibody. Immunoreactivity was detected with biotinylated secondary antibody, avidin biotin horseradish peroxidase complex (ABC) reagents, and diaminobenzidine as the chromogen (Vector Laboratories, Burlingame, Calif.) (Lam et al., J. Biol. Chem. 269:20648 (1994)). The tissue sections were counterstained with hematoxylin, preserved under coverglass, and examined by light microscopy.

Real Time Quantitative Reverse Transcriptase Polymerase Chain Reaction (RT-PCR) Assays:

Total RNA was isolated from liver tissue using TRIzol reagent (Invitrogen, Carlsbad, Calif.) according to the manufacturer's protocol. RNA concentrations and purity were determined from the absorbances measured at 260 nm and 280 nm. RNA (2 µg) was reverse transcribed using the AMV First Strand cDNA synthesis kit (Roche Diagnostics Corporation, Indianapolis, Ind.) and random oligodeoxynucleotide primers. Real time quantitative RT-PCR was used to measure mRNA levels of insulin, IGF-I, and IGF-II growth factors, their corresponding receptors, insulin receptor substrate (IRS) types 1, 2, and 4, and AAH, a downstream insulin/IGF-I responsive gene involved in cell motility and migration. Ribosomal 18S RNA levels measured in parallel reactions were used to calculate relative abundance of the mRNA transcripts (Myers et al., Proc. Natl. Acad Sci. USA 89:10350 (1992); Baltensperger et al., Science 260:1950 (1993); Yeon et al., Hepatology 38:703 (2003); Pares et al., Hepatology 12:1295 (1990)). PCR amplifications were performed in 25 µl reactions containing cDNA generated from 2.5 ng of original RNA template, 300 nM each of gene specific forward and reverse primer (Table 1), and 12.5 µl of 2× QuantiTect SYBR Green PCR Mix (Qiagen Inc., Valencia, Calif.). The amplified signals were detected continuously with the BIO-RAD iCycler iQ Multi-Color RealTime PCR Detection System (Bio-Rad, Hercules, Calif.). The amplification protocol used was as follows: initial 15-minutes denaturation and enzyme activation at 95° C., 45 cycles of 95° C.×15 sec, 55°-60° C.×30 sec, and 72° C.×30 sec. Annealing temperatures were optimized using the temperature gradient program provided with the iCycler software.

TABLE 1

Primer pairs for real time quantitative RT-PCR*

| Primer | Direction | Sequence (5'→3') | Position (mRNA) | Amplicon Size (bp) |
|---|---|---|---|---|
| 18S rRNA | For | GGA CAC GGA CAG GAT TGA CA (SEQ ID NO: 1) | 1278 | 50 |
| 18S rRNA | Rev | ACC CAC GGA ATC GAG AAA GA (SEQ ID NO: 2) | 1327 | |
| Insulin | For | TTC TAC ACA CCC AAG TCC CGT C (SEQ ID NO: 3) | 145 | 135 |
| Insulin | Rev | ATC CAC AAT GCC ACG CTT CTG C (SEQ ID NO: 4) | 279 | |
| Insulin Receptor | For | TGA CAA TGA GGA ATG TGG GGA C (SEQ ID NO: 5) | 875 | 129 |
| Insulin Receptor | Rev | GGG CAA ACT TTC TGA CAA TGA CTG (SEQ ID NO: 6) | 1003 | |
| IGF-1 | For | GAC CAA GGG GCT TTT ACT TCA AC (SEQ ID NO: 7) | 65 | 127 |
| IGF-I | Rev | TTT GTA GGC TTC AGC GGA GCA C (SEQ ID NO: 8) | 191 | |
| IGF-I Receptor | For | GAA GTC TGC GGT GGT GAT AAA GG (SEQ ID NO: 9) | 2138 | 113 |
| IGF-I Receptor | Rev | TCT GGG CAC AAA GAT GGA GTT G (SEQ ID NO: 10) | 2250 | |
| IGF-II | For | CCA AGA AGA AAG GAA GGG GAC C (SEQ ID NO: 11) | 763 | 95 |
| IGF-II | Rev | GGC GGC TAT TGT TGT TCA CAG C (SEQ ID NO: 12) | 857 | |
| IGF-II Receptor | For | TTG CTA TTG ACC TTA GTC CCT TGG (SEQ ID NO: 13) | 1066 | 91 |
| IGF-II Receptor | Rev | AGA GTG AGA CCT TTG TGT CCC CAC (SEQ ID NO: 14) | 1156 | |

In preliminary studies, SYBR Green-labeled PCR products were evaluated by agarose gel electrophoresis, and the authenticity of each amplicon was verified by nucleic acid sequencing. The complementary (c) DNAs were cloned into the PCRII vector (Invitrogen, Carlsbad, Calif.). Serial dilutions of known quantities of recombinant plasmid DNA containing the specific target sequences were used as standards in the PCR reactions, and the regression lines generated from the $C_t$ values of the standards were used to calculate mRNA abundance. Relative mRNA abundance was determined from the ng ratios of specific mRNA to 18S measured in the same samples (Myers et al., *Proc. Natl. Acad Sci. USA* 89:10350 (1992); Baltensperger et al., *Science* 260:1950 (1993)). Results were normalized to 18S because 18S is highly abundant and the levels were essentially invariant among the samples, whereas housekeeping genes were modulated with disease state. Inter-group statistical comparisons were made using the calculated mRNA/18S ratios. Control studies included real-time quantitative PCR analysis of: 1) template-free reactions; 2) RNA that had not been reverse transcribed; 3) RNA samples that were pre-treated with DNAse I; 4) samples treated with RNAse A prior to reverse transcriptase reaction; and 5) genomic DNA.

Receptor Binding Assays:

Fresh frozen tissue (~100 mg) was homogenized in 5 volumes of NP-40 lysis buffer (50 mM Tris-HCl, pH 7.5, 1% NP-40, 150 mM NaCl, 1 mM EDTA, 2 mM EGTA) containing protease inhibitors (1 mM PMSF, 0.1 mM TPCK, 1 µg/ml aprotinin, 1 µg/ml pepstatin A, 0.5 µg/ml leupeptin, 1 mM NaF, 1 mM $Na_4P_2O_7$). Protein concentrations were determined using the bicinchoninic acid (BCA) assay (Pierce, Rockford, Ill.). Exploratory studies determined the amounts of protein and concentrations of radiolabeled ligand required to achieve 20% specific binding. Insulin receptor binding assays were performed using 100 µg protein. IGF-I binding assays required 25 µg protein per sample, and IGF-II receptor binding assays were optimized using 10 µg protein. Competitive equilibrium binding assays were used to assess growth factor binding in relation to ethanol exposure. For total binding, duplicate individual protein samples were incubated in 100 µl reactions containing binding buffer (100 mM HEPES, pH 8.0, 118 mM NaCl, 1.2 mM $MgSO_4$, 8.8 mM dextrose, 5 mM KCl, 1% bovine serum albumin) and 100 nCi/ml of [$^{125}$I] (2000 Ci/mmol; 50 pM) insulin, IGF-I, or IGF-II. To measure non-specific binding, replicate samples were identically prepared but with the addition of 0.1 µM unlabeled (cold) ligand.

All reactions were performed in 1.5 ml Eppendorff tubes, and the incubations were performed at 4° C. for 16 hours with gentle platform agitation. Bound radiolabeled tracer was then precipitated by adding 500 µl of 0.15% bovine gamma globulin (prepared in 100 mM Tris-HCl, pH 8.0) followed by 400 µl 37.5% polyethylene glycol 8000 (PEG-8000; prepared in 100 mM Tris-HCl, pH 8.0) to each tube. The samples were thoroughly mixed by vortexing, and then incubated on ice for at least 2 hours. The precipitates were collected by centrifuging the samples at 15,000×g for 5 minutes at room temperature. The supernatant fraction, which contained unbound (free) ligand, was transferred in its entirety to a Gamma counting tube (Sarstedt, Newton, N.C.). The Eppendorff tube tip containing the pellet was cut and released directly into a separate Gamma counting tube. The samples were counted for 1 minute in an LKB CompuGamma CS Gamma counter. Specific binding was calculated by subtracting fmol of non-specific binding, i.e., amount bound in the presence of cold ligand, from the total fmol bound (absence of unlabeled competitive ligand). The results were analyzed and plotted using the GraphPad Prism 4 software (GraphPad Software, Inc., San Diego, Calif.).

Source of Reagents:

Human recombinant [$^{125}$I] Insulin, IGF-I, and IGF-II were purchased from Amersham Biosciences (Piscataway, N.J.). Unlabeled human insulin was purchased from Sigma-Aldrich (St. Louis, Mo.). Recombinant IGF-I and IGF-II were obtained from Bachem (King of Prussia, Pa.). Monoclonal antibodies to 8-OHdG and HNE were purchased from Oxis Scientific. All other fine chemicals and reagents were purchased from CalBiochem (Carlsbad, Calif.) or Sigma-Aldrich (St. Louis, Mo.).

Statistical Analysis:

Experiments were conducted using 9 rats per group. Data are depicted as means±S.E.M. in the graphs. Inter-group comparisons were made using Student T-tests. Statistical analyses were performed using the Number Cruncher Statistical System (Kaysville, Utah). P-values corresponding to significant differences and trends are indicated over the graphs.

Effects of Chronic Alcohol Feeding on Liver Structure and Gene Expression

Chronic ethanol feeding produced striking alterations in liver-histology as shown in FIG. 1 (top panels). In the ethanol fed group, there is prominent lipid accumulation in hepatocytes. More important, there are areas of hepatocyte damage, cell dropout and necrosis (inset). The lobular architecture is distorted and areas of inflammation and inflammatory cell infiltrates are evident. This picture is consistent with the liver damage seen in humans with ALD. The middle panels of FIG. 1 illustrate lipid peroxidation induced by chronic ethanol exposure as demonstrated by HNE staining. In addition, there is extensive DNA damage to hepatocytes as shown by 8-OHdG immunoreactivity (bottom panels). Therefore, chronic ethanol exposure generates oxidative stress and DNA alterations in the liver as two principle mechanisms of cellular injury.

Figure 2:
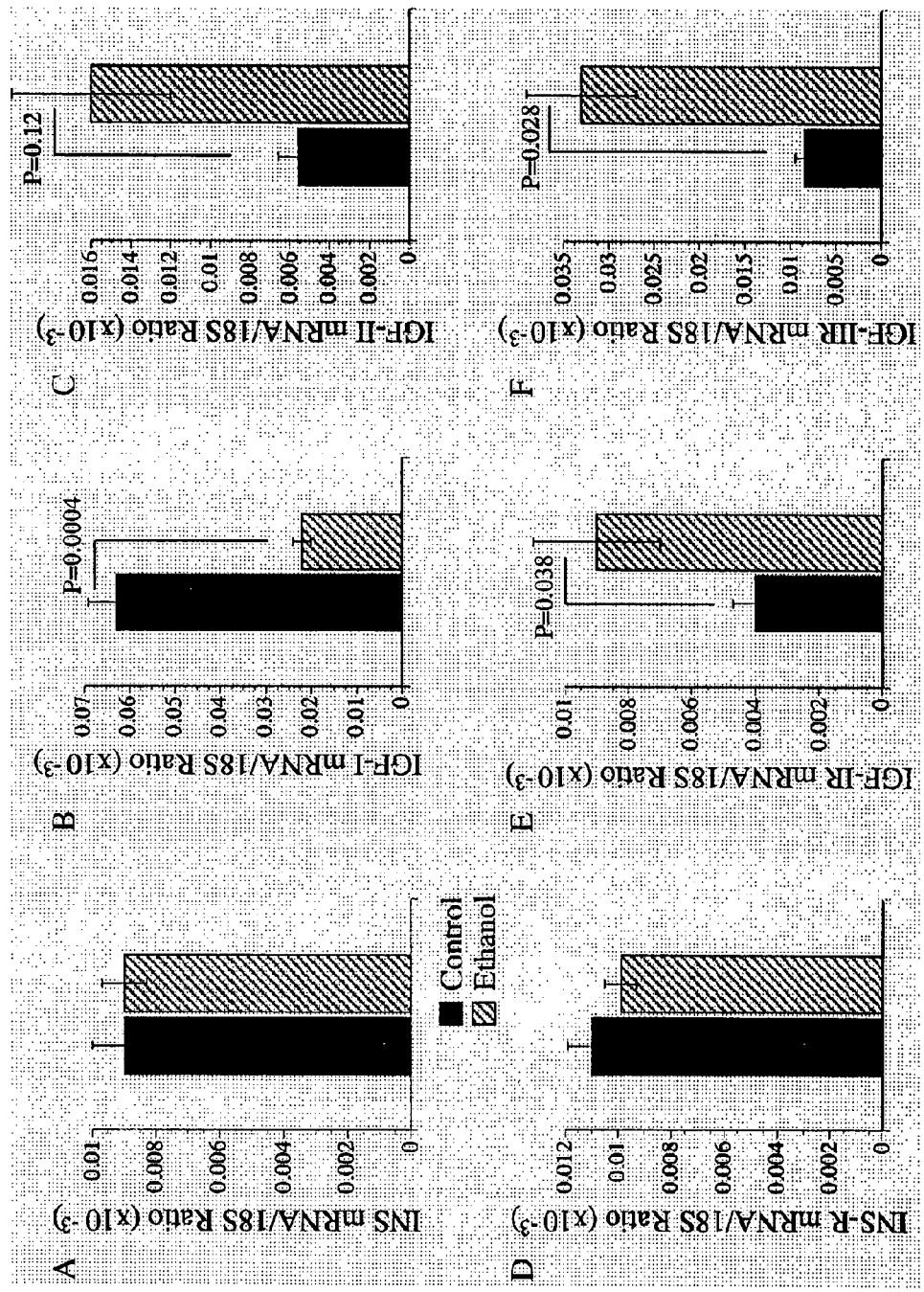
Figure 3:
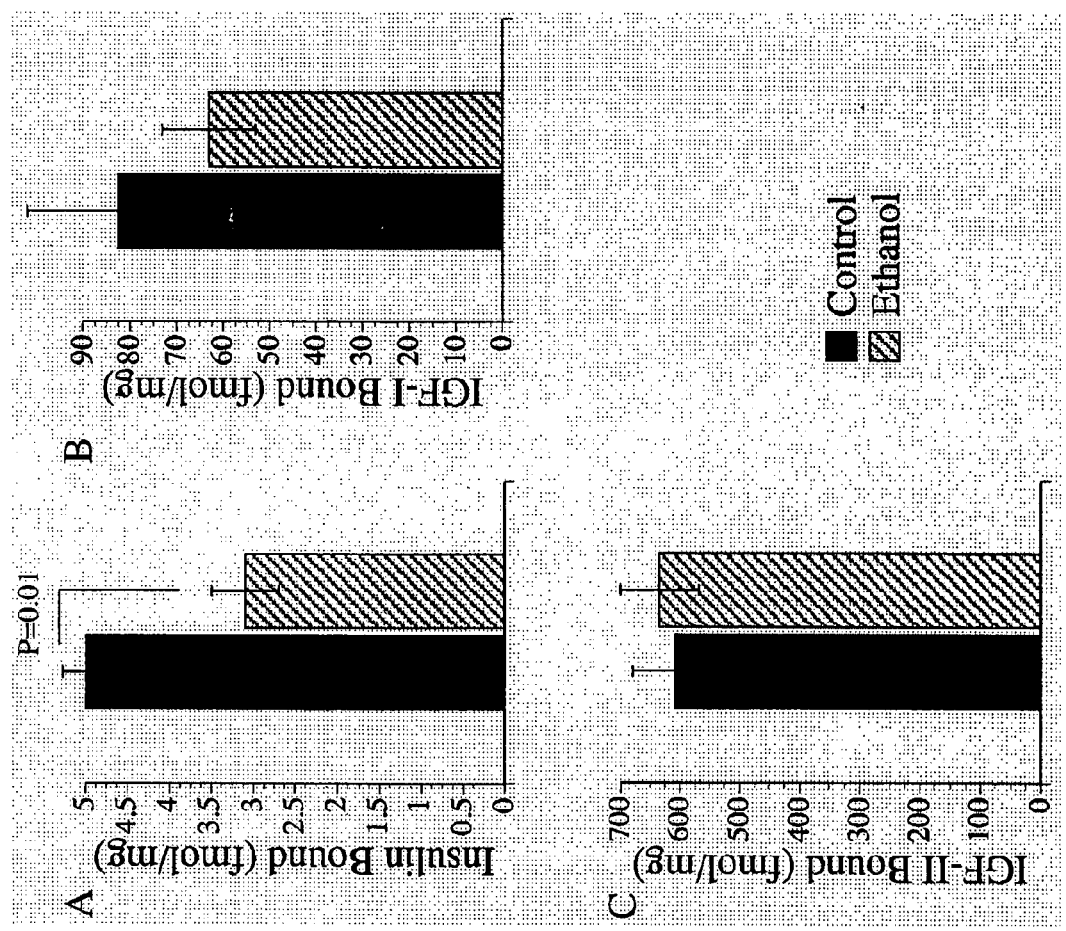
Figure 4:
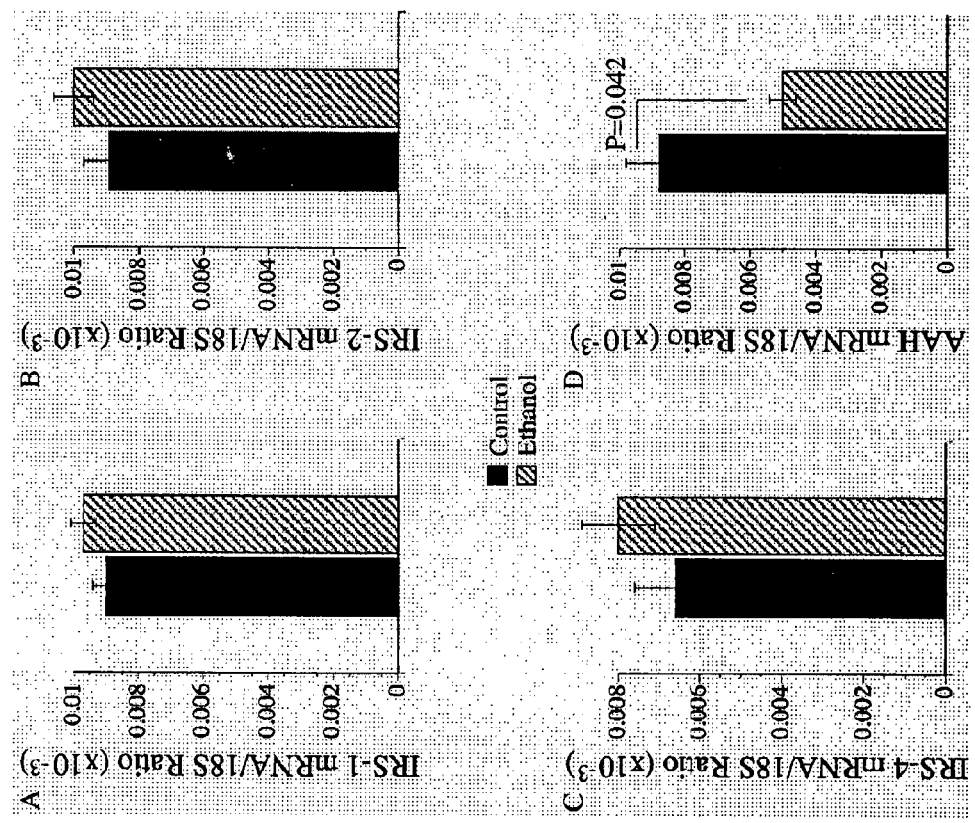

The ethanol effects on insulin signaling in the liver were determined by real time PCR as shown in FIG. 2. There was no-difference in insulin gene expression comparing ethanol exposed liver to control (2A). However, there was a striking reduction in IGF-I gene expression (p=0.0004) in the liver derived from chronic ethanol fed rats (2B). In contrast, IGF-II expression was increased in ethanol compared to control liver (2C). Likewise, insulin receptor (INS-R) levels were similar to control and IGF-I and IGF-II receptor gene expression was increased in alcohol fed groups (2D-2F). The major change in insulin signaling involved reduced insulin binding to its receptor as shown in FIG. 3A. This would create insulin resistance in the liver since the levels of IRS-1, 2 and 4 were no different comparing ethanol to controls as shown in FIGS. 4A-4C. In support of this concept is the reduced AAH expression which is a downstream insulin responsive gene in the liver derived from chronic ethanol fed rats (4D). Thus, a state of insulin resistance is produced with a major defect in insulin binding to the receptor which would impair all insulin signaling events since it alters the initial step (i.e., ligand-receptor interaction) high up in the signal transduction cascades.

Effect of Chronic Alcohol Feeding on Liver Regeneration

Figure 5:
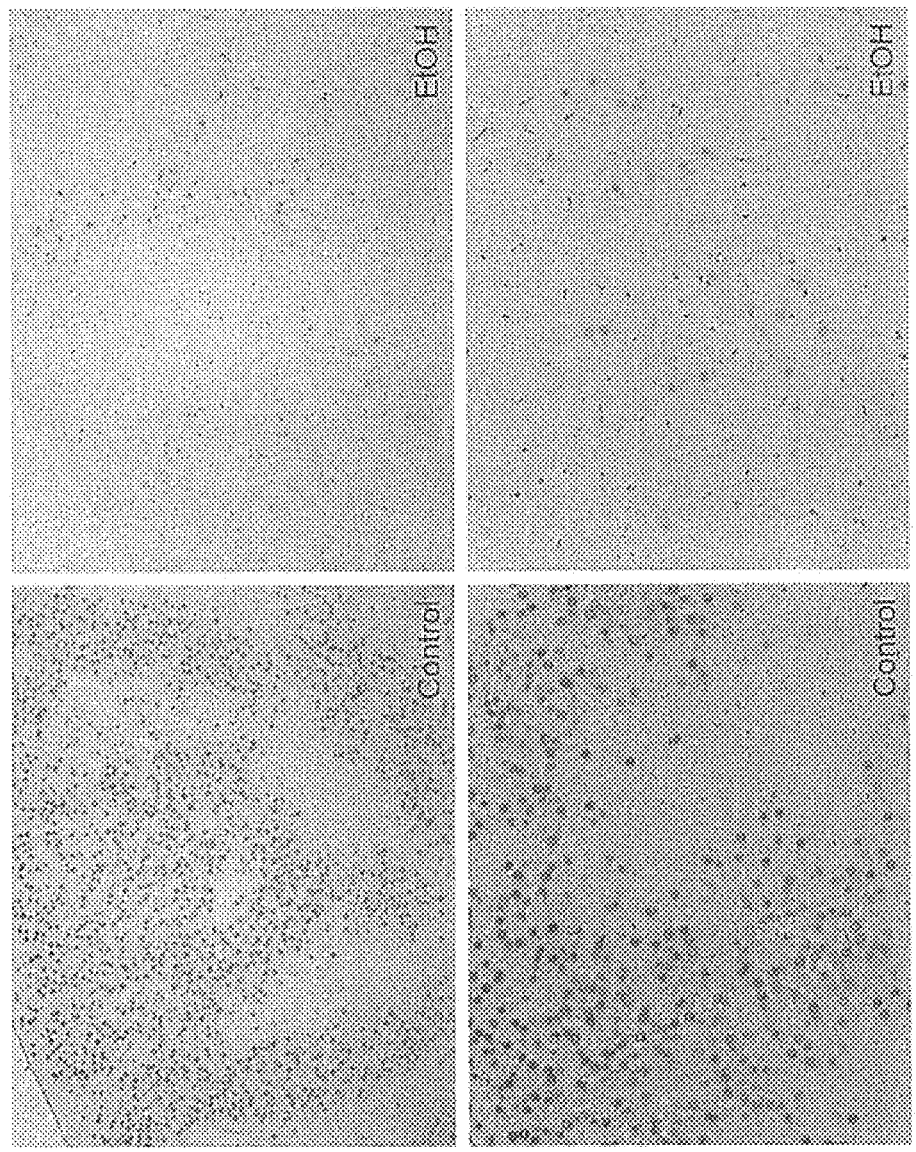
Figure 6:
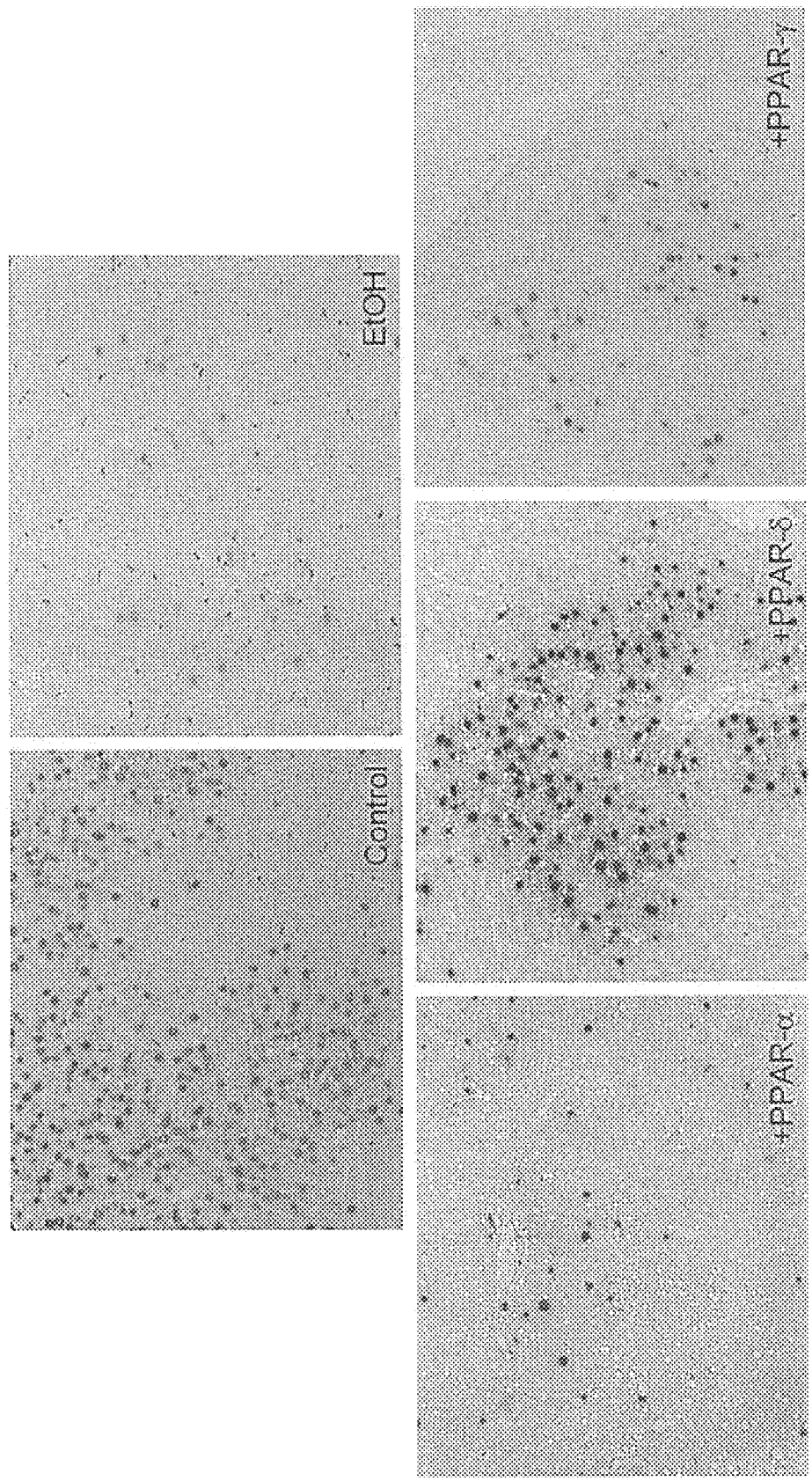

FIG. 5 shows the striking effect of chronic ethanol feeding on the hepatic regenerative response as measured by BrdU immunostaining at 24 hours after ⅔ hepatectomy. Note the robust uptake of BrdU in hepatocytic nuclei of control animals in over 60% of the cells (left hand panels) as compared to less than 10% in the ethanol fed group (right hand panels). These results confirm the adverse role of ethanol on the hepatic repair process. In contrast, as shown in FIG. 6, there is PPAR agonist rescue of ethanol impaired DNA synthesis. Note that PPAR-α (lower left hand panel) and PPAR-γ (lower right hand panel) show a modest increase in BrdU labeling of approximately 20% compared to ethanol fed animals. It was unexpected and surprising that PPAR-δ treatment of chronic ethanol fed rats essentially restored liver regeneration to levels seen in normal control animals after ⅔ hepatectomy.

Figure 7:
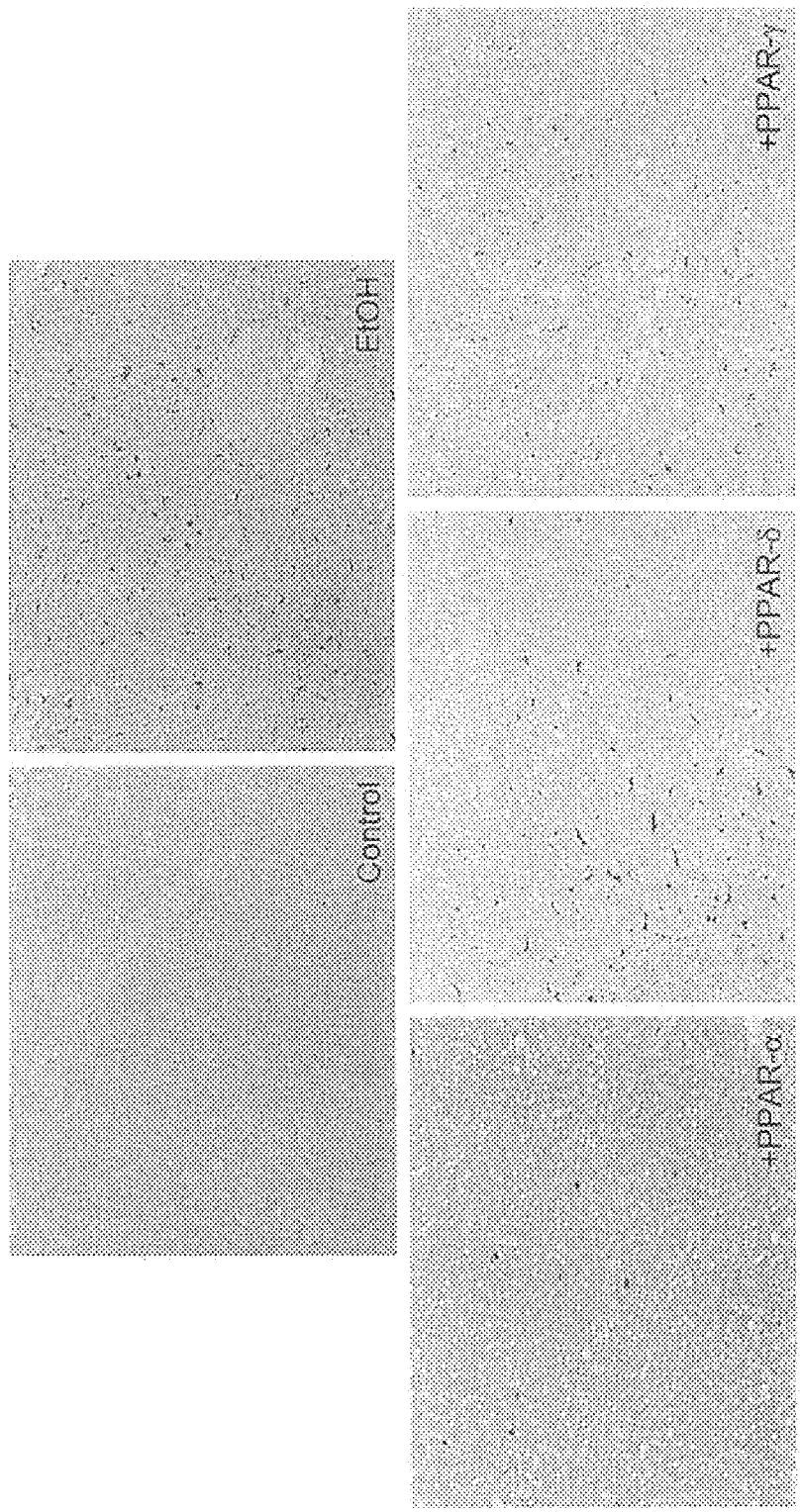
FIG. 7 shows evidence that PPAR agonists rescue chronic ethanol effects on lipid peroxidation as measured by HNE immunoreactivity. Note that α, γ and δ PPAR agents work equally well in preventing cell damage in the liver.
Figure 8:
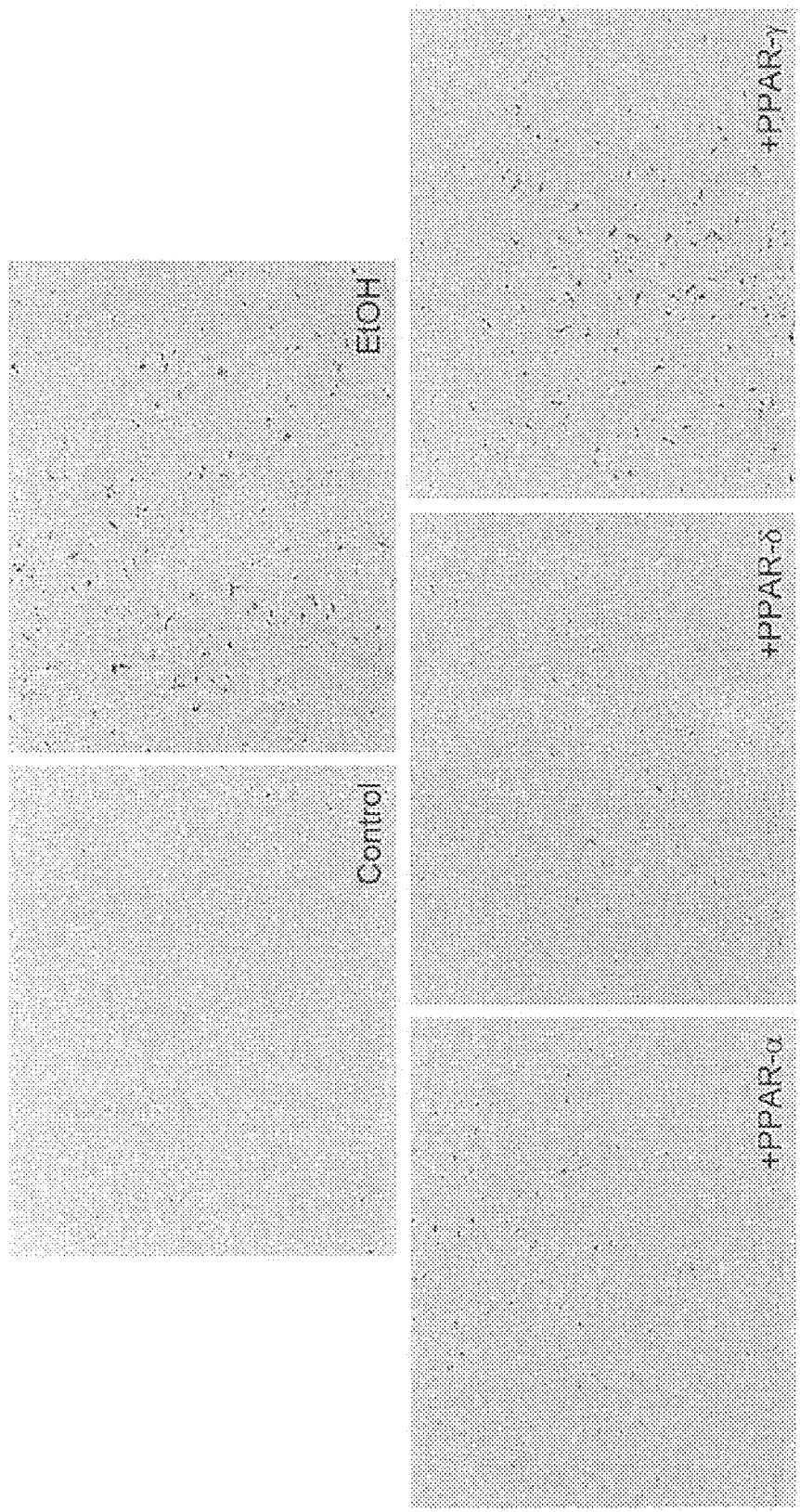
FIG. 8 shows DNA damage produced by chronic ethanol consumption is attenuated by PPAR agonists. Note that PPAR-δ is superior to the α and γ agents in preventing hepatocyte damage.

Taken together, these studies demonstrate that chronic ethanol consumption leads to hepatocyte injury and inflammation as well as oxidative stress and DNA damage to the liver. The capacity of the liver to regenerate is substantially impaired. These PPAR agonists have also been examined to determine if they rescue injury from lipid peroxidation as shown in FIG. 7. Indeed, PPAR agonists substantially improved chronic ethanol induced hepatic lipid peroxidation as measured by HNE immunostaining with all three classes (α, γ, and δ) being equally effective. Moreover, with respect to DNA damage produced by ethanol as shown in FIG. 8, PPAR-δ showed the most prominent protective effect followed by PPAR-α and, PPAR-γ. Therefore, these agents attack the two major pathologic features of ALD, namely, ongoing liver damage and inhibition of the repair process. It is anticipated that such agents will improve the outcome of individuals with ALD by preventing or slowing the liver damage produced by chronic alcohol abuse while stimulating or restoring the hepatic regenerative response.

Example 2

General Methods
Chronic Ethanol Exposure Model:

Adult male (~200-250 g) Long Evans rats (Harlan Sprague Dawley, Inc., Indianapolis, Ind.) were pair-fed with isocaloric liquid diets (BioServ, Frenchtown, N.J.) containing 0% (control) or 37% ethanol by caloric content (9.2% v/v) for 8 weeks. During the week prior to initiating the experiment, rats were adapted to the ethanol-containing diets by sequentially feeding them for two days each with diets containing 8%, 17%, 24%, and then 37% ethanol. Chow fed control rats were also studied. Rats were monitored daily to ensure equivalent food consumption and maintenance of body weight. During the last 3 weeks of the experiment while being maintained on either the 0% or 37% ethanol-containing liquid diets, rats in both groups were administered twice weekly (Mondays and Thursdays) intraperitoneal (i.p.) injections of vehicle (saline), a PPAR-α (GW7647; 25 µg/kg), PPAR δ (L-165,041; 2 µg/kg), or PPAR-γ (F-L-Leu; 20 µg/kg) agonist (CalBiochem, Carlsbad, Calif.). At the conclusion of the experiment, rats were anesthetized with vaporized isofluorane (SurgiVet, Inc. Waukesha, Wis.), and liver and blood were harvested for analysis. Liver tissue samples were immersion fixed in Histochoice (Amresco Corp., Solon, Ohio) and embedded in paraffin. Adjacent histological sections were stained with Hematoxylin and Eosin or Gomori's Trichrome and examined under code. In addition, liver tissue samples were snap-frozen in a dry ice methanol bath and then stored at −80° C. for later mRNA and protein studies. Throughout the experiment, rats were housed under humane conditions and kept on a 12-hour light/dark cycle with free access to food. All experiments were performed in accordance with protocols that conform to guidelines established by the National Institutes of Health and were approved by Institutional Animal Care and Use Committee at the Lifespan-Rhode Island Hospital.

Analysis of mRNA:

Total RNA was extracted from liver tissue using TRIzol® reagent (Invitrogen, Carlsbad, Calif.) according to the manufacturer's protocol. RNA concentrations and purity were determined from the absorbances measured at 260 nm and 280 nm. RNA (2 µg) was reverse transcribed using the AMV First Strand cDNA synthesis kit (Roche Diagnostics Corporation, Indianapolis, Ind.) and random oligodeoxynucleotide primers. Quantitative reverse transcriptase polymerase chain reaction (qRT-PCR) assays were used to measure steady-state levels of specific mRNA transcripts. PCR amplifications were performed in 20 µl reactions containing cDNA generated from 2.5 ng of original RNA template, 300 nM each of gene specific forward and reverse primer (Table 2), and 10 µl of 2× QuantiTect SYBR Green PCR Mix (Qiagen Inc, Valencia, Calif.). The amplified signals were detected continuously with the Mastercycler ep realplex instrument and software (Eppendorf AG, Hamburg, Germany). The amplification protocol used was as follows: initial 15-minutes denaturation and enzyme activation at 95° C., 45 cycles of 95° C.×15 sec, 55°-60° C.×30 sec, and 72° C.×30 sec. Annealing temperatures were optimized using the temperature gradient program provided with the Mastercycler ep realplex software.

TABLE 2

Primer pairs for quantitative PCR*

| Primer | Direction | Sequence (5'→3') | Position (mRNA) | Amplicon Size (bp) |
|---|---|---|---|---|
| Albumin | For | CTT CAA AGC CTG GGC AGT AG (SEQ ID NO: 15) | 702 | 188 |
| Albumin | Rev | TGG AGA TAG TGG CCT GGT TC (SEQ ID NO: 16) | 889 | |
| ASBT | For | GCA TTG GCA TTT CTC TGG TT (SEQ ID NO: 17) | 598 | 181 |
| ASBT | Rev | GGT TCA ATG ATC CAG GCA CT (SEQ ID NO: 18) | 778 | |
| KCR | For | TCA CAA ATG CTG TGG ACC AT (SEQ ID NO: 19) | 1427 | 161 |
| KCR | Rev | GTC TTC ACG CTC TCC GTT TC (SEQ ID NO: 20) | 1587 | |
| GFAP | For | GGT GGA GAG GGA CAA TCT CA (SEQ ID NO: 21) | 433 | 215 |
| GFAP | Rev | CTC GAA CTT CCT CCT CAT GG (SEQ ID NO: 22) | 647 | |
| Desmin | For | ACC TGC GAG ATT GAT GCT CT (SEQ ID NO: 23) | 1069 | 206 |
| Desmin | Rev | ACA TCC AAG GCC ATC TTC A (SEQ ID NO: 24) | 1274 | |
| Col1a2 (Collagen) | For | ACC TCA GGG TGT TCA AGG TG (SEQ ID NO: 25) | 1623 | 222 |
| Col1a2 (Collagen) | Rev | CGG ATT CCA ATA GGA CCA GA (SEQ ID NO: 26) | 1844 | |
| Insulin | For | TTC TAC ACA CCC AAG TCC CGT C (SEQ ID NO: 3) | 145 | 135 |
| Insulin | Rev | ATC CAC AAT GCC ACG CTT CTG C (SEQ ID NO: 4) | 279 | |
| Insulin Receptor | For | TGA CAA TGA GGA ATG TGG GGA C (SEQ ID NO: 5) | 875 | 129 |
| Insulin Receptor | Rev | GGG CAA ACT TTC TGA CAA TGA CTG (SEQ ID NO: 6) | 1003 | |
| IGF-I | For | GAC CAA GGG GCT TTT ACT TCA AC (SEQ ID NO: 7) | 65 | 127 |

TABLE 2-continued

Primer pairs for quantitative PCR*

| Primer | Direction | Sequence (5'→3') | Position (mRNA) | Amplicon Size (bp) |
|---|---|---|---|---|
| IGF-I | Rev | TTT GTA GGC TTC AGC GGA GCA C (SEQ ID NO: 8) | 191 | |
| IGF-I Receptor | For | GAA GTC TGC GGT GGT GAT AAA GG (SEQ ID NO: 9) | 2138 | 113 |
| IGF-I Receptor | Rev | TCT GGG CAC AAA GAT GGA GTT G (SEQ ID NO: 10) | 2250 | |
| IGF-II | For | CCA AGA AGA AAG GAA GGG GAC C (SEQ ID NO: 11) | 763 | 95 |
| IGF-II | Rev | GGC GGC TAT TGT TGT TCA CAG C (SEQ ID NO: 12) | 857 | |
| IGF-II Receptor | For | TTG CTA TTG ACC TTA GTC CCT TGG (SEQ ID NO: 13) | 1066 | 91 |
| IGF-II Receptor | Rev | AGA GTG AGA CCT TTG TGT CCC CAC (SEQ ID NO: 14) | 1156 | |
| IRS-1 | For | GAT ACC GAT GGC TTC TCA GAC G (SEQ ID NO: 27) | 604 | 134 |
| IRS-1 | Rev | TCG TTC TCA TAA TAC TCC AGG CG (SEQ ID NO: 28) | 737 | |
| IRS-2 | For | CAA CAT TGA CTT TGG TGA AGG GG (SEQ ID NO: 29) | 255 | 109 |
| IRS-2 | Rev | TGA AGC AGG ACT ACT GGC TGA GAG (SEQ ID NO: 30) | 363 | |
| IRS-4 | For | ACC TGA AGA TAA GGG GTC GTC TGC (SEQ ID NO: 31) | 2409 | 132 |
| IRS-4 | Rev | TGT GTG GGG TTT AGT GGT CTG G (SEQ ID NO: 32) | 2540 | |
| GAPDH | For | AGT GGG CAT CAA TGG ATT TGG (SEQ ID NO: 33) | 306 | 241 |
| GAPDH | Rev | GGG GAT TTC CTT AGG TTC TTT GC (SEQ ID NO: 34) | 546 | |
| AAH | For | TGC CTG CTC GTC TTG TTT GTG (SEQ ID NO: 35) | 666 | 118 |
| AAH | Rev | ATC CGT TCT GTA ACC CGT TGG (SEQ ID NO: 36) | 783 | |

In preliminary studies, SYBR Green-labeled PCR products were evaluated by agarose gel electrophoresis, and authenticity was verified by nucleic acid sequencing. Complementary (c) DNAs were cloned into PCR-II vectors (Invitrogen, Carlsbad, Calif.). In addition, melt-curve analyses demonstrated the presence of a single PCR product without formation of primer-dimer peaks. Serial dilutions of recombinant plasmid DNA containing target sequences were used as standards in PCR reactions, and regression lines generated from the $C_t$ values of the standards were used to calculate mRNA abundance. Relative mRNA expression was expressed as the ng ratio of specific mRNA to ribosomal (r) 18S measured in the same samples because 18S is highly abundant and the levels are not modulated with disease state. Statistical comparisons were made using the calculated mRNA/18S ratios. Control studies included analysis of: 1) template-free reactions; 2) RNA that had not been reverse transcribed; 3) RNA samples that were pre-treated with DNAse I; 4) samples treated with RNAse A prior to the reverse transcriptase reaction; and 5) genomic DNA.

Receptor Binding Assays:

Saturation binding studies were used to determine if the PPAR agonist treatments improved ethanol-impaired insulin and IGF receptor binding in liver. Fresh frozen liver tissue was homogenized in 5 volumes of lysis buffer containing 50 mM Tris-HCl, pH 7.5, 1% NP-40, 150 mM NaCl, 1 mM EDTA, 2 mM EGTA, plus protease (1 mM PMSF, 0.1 mM TPCK, 1 µg/ml aprotinin, 1 µg/ml pepstatin A, 0.5 µg/ml leupeptin, 1 mM NaF, 1 mM $Na_4P_2O_7$) and phosphatase (2 mM $Na_3VO_4$) inhibitors. Protein concentration was determined using the bicinchoninic acid (BCA) assay (Pierce, Rockford, Ill.). Exploratory studies determined the optimum amounts of protein and concentrations of radiolabeled ligand required to achieve 20% specific binding. Insulin receptor binding was measured using 100 µg protein per assay tube. IGF-I binding assays required 25 µg protein per sample, and IGF-II receptor binding assays required 10 µg protein per reaction.

To generate the binding curse, samples from 8 rats per group were pooled in equivalent ratios and protein concentrations were adjusted to be identical for each group. For total binding, duplicate samples were incubated in 100 µl reactions containing binding buffer (100 mM HEPES, pH 8.0, 118 mM NaCl, 1.2 mM $MgSO_4$, 8.8 mM dextrose, 5 mM KCl, 1% bovine serum albumin) and 0.0031 to 1 µCi/ml of [$^{125}$I] (2000 Ci/mmol) insulin, IGF-I, or IGF-II. For non-specific binding, duplicate samples were identically prepared but with the addition of 0.1 µM unlabeled (cold) ligand. Incubations were carried out for 16 hours at 4° C. in non-binding 96 well plates (Corning Incorporated Life Science, Lowell, Mass.). Reactions were vacuum harvested (Corning, Lowell, Mass.) onto 96-well GF/C filter plates that had been presoaked for 30 minutes in 0.33% polyethyleneimine (PEI) solution. The filters were washed 5 times with buffer containing 50 mM buffer [4-2-hydroxyethyl)-1-piperazine-ethanesulfonic acid (HEPES), pH 7.4, 500 mM NaCl, and 0.1% BSA. After drying, 50 µl Microscint-20 (Packard Instrument Company, Meriden, Conn.) was added to each well and the levels of bound [$^{125}$I] insulin, IGF-I, or IGF-II were measured in a TopCount machine (Packard Instrument Company, Meriden, Conn.). Specific binding was calculated by subtracting fmol/mg of non-specifically bound isotope, i.e., amount bound in the presence of cold ligand, from the total fmol/mg bound isotope. The data were analyzed and graphed using GraphPad Prism 5 software (GraphPad Software, Inc., San Diego, Calif.).

Protein Studies:

Protein expression was examined by Western blot analysis or enzyme-linked immunosorbant assay (ELISA). Western blot analysis was used to measure AAH and GAPDH expression. In addition, immunoreactivity corresponding to the p85 subunit of PI3 kinase was measured as a negative (loading) control. For Western blot analysis, liver tissue was homogenized in 5 volumes of radio-immunoprecipitation assay (RIPA) buffer (50 mM Tris-HCl, pH 7.5, 1% NP40, 0.25% Na-deoxycholate, 150 mM NaCl, 1 mM EDTA, 2 mM EGTA) containing protease (1 mM PMSF, 0.1 mM TPCK, 1 mg/ml aprotinin, 1 mg/ml pepstatin A, 0.5 mg/ml leupeptin, 1 mM NaF, 1 mM $Na_4P_2O_7$) and phosphatase (2 mM $Na_3VO_4$) inhibitors. Protein concentrations were determined using the BCA assay (Pierce, Rockford, Ill.). Samples containing 20 µg of protein were fractionated by SDS-PAGE and transferred to PVDF membranes. Non-specific binding sites were blocked with SuperBlock-TBS (Pierce, Rockford, Ill.), and membranes were incubated with primary antibody (0.5-1 µg/ml) overnight at 4° C. with gentle platform agitation. Immunoreactivity was detected with horseradish peroxidase (HRP) conjugated secondary antibody, enhanced chemiluminescence (ECL) reagents (Pierce, Rockford, Ill.), and the Kodak Digital Science Imaging Station (NEN Life Sciences, Boston, Mass.).

ELISAs were used to measure immunoreactivity corresponding to AAH, GAPDH and β-actin (negative control). ELISAs were performed in 96-well opaque polystyrene plates (Nalge Nunc International, Rochester, N.Y.). RIPA protein extracts diluted in TBS (40 ng/100 µl) were adsorbed to the bottoms of the wells by overnight incubation at 4° C. After rinsing in TBS, the wells were blocked for 4 hours with 250 µl/well of 2% BSA in TBS. The proteins were then incubated with primary antibody (0.01-0.1 µg/ml) for 1 hour at room temperature. Immunoreactivity was detected with HRP-conjugated secondary antibody (1:10000; Pierce) and the Amplex Red soluble fluorophore (Molecular Probes). Amplex Red fluorescence was measured (Ex 530/Em 595) in an M-5 machine (fluorescence light units; FLU). Binding specificity was determined from parallel negative control incubations with non-relevant antibodies, or with the primary or secondary antibody omitted. The mean levels of specific AAH, GAPDH, and β-actin immunoreactivity were used for inter-group statistical comparisons.

Source of Reagents:

The PPAR agonists, GW7647 (PPAR-α), L165, 041 (PPAR-δ), and Fmoc-Leu (PPAR-γ) were purchased from Calbiochem (Tecumsula, Calif.). Human recombinant [$^{125}$I] Insulin, IGF-I, and IGF-II were purchased from Amersham Biosciences (Boston, Mass.). Unlabeled human insulin, recombinant IGF-I, and recombinant IGF-II were purchased from Bachem (Torrance, Calif.). QuantiTect SYBR Green PCR Mix was obtained from Qiagen Inc (Valencia, Calif.). Monoclonal antibodies to GAPDH and β-actin were purchased from Chemicon (Tecumsula, Calif.). The A85G6 mouse monoclonal antibody used to detect AAH was generated with purified recombinant human protein. All other fine chemicals were purchased from CalBiochem (Carlsbad, Calif.) or Sigma-Aldrich (St. Louis, Mo.).

Statistical Analysis:

Data depicted in graphs represent the mean±S.E.M. or mean±95% C.I.L. for each group. Inter-group comparisons were made using repeated measures analysis of variance (ANOVA) and the post-hoc Tukey-Kramer test for significance. Statistical analyses were performed using GraphPad Prism 5 software (GraphPad Software, Inc., San Diego, Calif.).

PPAR Agonists Reverse Ethanol-Induced Liver Pathology:

Livers from rats fed with either control liquid diet or chow showed the expected well-organized lobular architecture with minimal evidence of steatosis, variation in nuclear size, or hepatocyte drop-out (FIGS. 9A, 9E, 9I). In contrast, ethanol exposed livers exhibited microvesicular and macrovesicular steatosis with multiple foci of intralobular lymphomononuclear cell inflammation and scattered areas of apoptosis and/or necrosis (FIGS. 10A, 10E, 10I). In addition, chronic ethanol feeding resulted in hepatic architectural disarray with loss of regular chords and increased variability in size of hepatocyte nuclei. There was no evidence of increased fibrosis, regenerating nodule formation, or cirrhosis in ethanol-exposed livers. Control rats treated with the PPAR-α agonist had no detectable histological changes in liver (FIGS. 9B, 9F, 9J) relative to vehicle-treated controls. In contrast, control rats treated with the PPAR-δ (FIGS. 9C, 9G, 9K) or PPAR-γ (FIGS. 9D, 9H, 9L) agonist had less well-organized hepatic architecture due to sinusoidal widening and apparently increased hepatocyte crowding. In addition, PPAR-δ or PPAR-γ treatment resulted in increased nuclear prominence and micro-vacuolation of the cytoplasm of hepatocytes. The micro-vacuolation was associated with increased periodic-acid Schiff (PAS) staining, consistent with increased glycogen accumulation. In the ethanol-fed group, treatment with a PPAR agonist had variable but distinct effects on liver histology in terms of reducing the architectural disarray, steatosis, and cell death caused by chronic ethanol exposure (FIG. 10). Treatment with the PPAR-α, PPAR-δ, or PPAR-γ agonist reduced the disordered architecture and resulted in more of a chord-like arrangement of hepatocytes, and the extents of both micro- and macrosteatosis were overtly reduced. Nonetheless, small foci of necrosis (FIG. 10J, insets), inflammation (FIG. 10G, inset and FIG. 10H, arrow), and apoptosis (FIG. 10L, inset) were readily detected, although these lesions were generally less conspicuous than in the vehicle-treated, ethanol-exposed livers. The most striking improvements in liver histology occurred in ethanol-fed rats that had been treated with the PPAR-δ (FIGS. 10C and 10K) or PPAR-γ (FIGS. 10D and 10L) agonist.

General Comments Regarding qRT-PCR Studies:

The use of qRT-PCR enabled all samples to be analyzed simultaneously and with sufficient replicates to demonstrate consistency of results. With the techniques employed, the quality of cDNA generated from tissue was judged to be excellent based on the similar 18S $C_t$ values and consistent 28S:18S ratios obtained for livers of control ethanol-fed rats, irrespective of PPAR agonist treatment. The use of qRT-PCR was ideally suited for rigorous analysis of gene expression because the amplicons were small (mainly <150 bp), thereby circumventing potential problems related to partial RNA degradation, e.g., nicking, which often occurs with chronic ethanol exposure and oxidative stress. Specificity of the amplified products was verified by direct nucleic acid sequencing. Control studies in which cDNA templates were excluded, RNA was not reverse transcribed, RNA samples were pre-treated with RNAse A prior to the RT step, or genomic DNA was used in reactions, produced no detectable amplified products as demonstrated by qPCR analysis and agarose gel electrophoresis. Treatment of RNA samples with DNAse I prior to the RT step had no effect on the detection levels of amplified gene products.

PPAR Agonist Treatments Alter Cell Population Profiles in Liver:

Liver mRNA levels of albumin, apical sodium-dependent bile transporter protein (ASBT), glial fibrillary acidic protein (GFAP), Kupffer cell receptor (KCR), desmin, and collagen were measured by qRT-PCR. Albumin expression was used as an index of hepatocyte abundance/function. ASBT reflects bile duct epithelium. GFAP is an early marker of stellate cell activation and desmin marks transdifferentiation of hepatic stellate cells into myofibroblasts. KCR is a maker of Kupffer cells and increased expression could reflect an intra-hepatic response to injury. Collagen gene expression corresponds to fibrogenic potential or active fibrogenesis. Altogether, these assessments of gene expression in liver, which we have termed "cell profiling," enabled us to quantify ethanol and PPAR agonist associated relative shifts in liver cell type and function.

Figure 11:
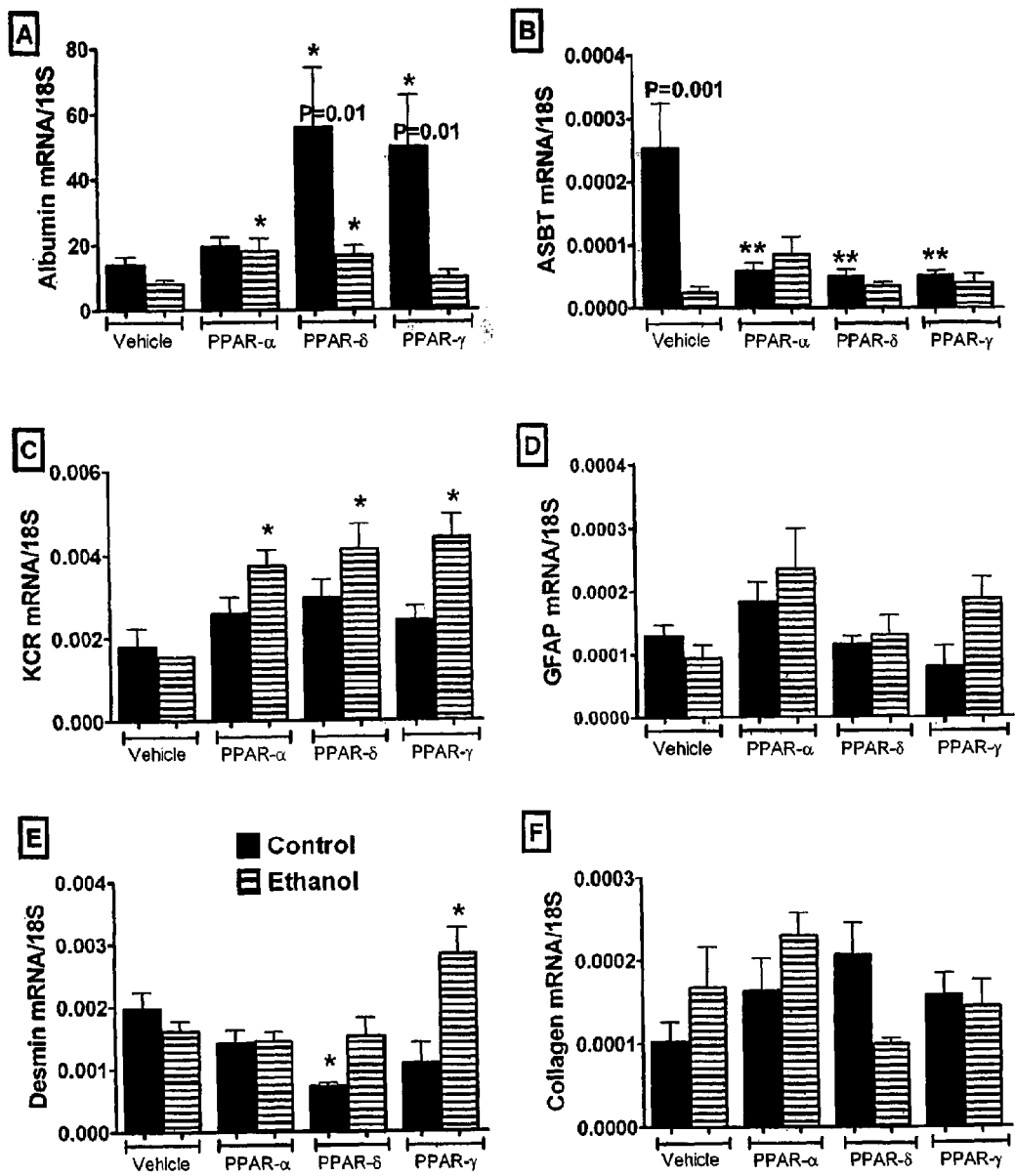
FIGS. 11A-11F show the effects of PPAR agonists on liver cell profiles in control and ethanol-fed animals.

Livers of vehicle-treated control rats had significantly higher mean levels of albumin mRNA compared with livers from vehicle-treated ethanol-exposed rats (FIG. 11A). Treatment with the PPAR-δ or PPAR-γ, but not the PPAR-α agonist significantly increased the mean levels of albumin mRNA in control livers. In the ethanol-fed group, treatment with the PPAR-α or PPAR-δ agonist significantly increased albumin expression relative to vehicle-treated ethanol-fed rats, but not relative to any of the control groups. PPAR-γ treatment did not significantly alter albumin expression in ethanol-exposed livers.

ASBT expression was highest in vehicle-treated control livers, and each of the PPAR-agonist treated control livers had a significantly lower mean level of ASBT compared with the vehicle-treated controls (FIG. 11B). Livers from vehicle-treated, ethanol-exposed rats had significantly lower mean levels of ASBT expression relative to the corresponding control group. In ethanol-fed rats, PPAR-α agonist treatment significantly increased hepatic ASBT expression relative to vehicle, but not relative to any of the control diet fed rats. PPAR-δ or PPAR-γ treatment did not significantly alter ASBT mRNA levels in ethanol-exposed livers.

KCR expression was lowest in vehicle-treated control and ethanol-exposed livers. Treatment with the PPAR-α, PPAR-δ, or PPAR-γ agonists increased the mean levels of KCR mRNA in both control and ethanol-exposed livers; however, the differences from corresponding vehicle-treatment were only statistically significant for ethanol-fed rats (FIG. 11C). PPAR-α, PPAR-δ, and PPAR-γ treatments produced similar degrees of increased KCR expression in ethanol-exposed livers. However, KCR expression was significantly higher in ethanol-exposed relative to control only in the PPAR-γ treatment groups.

GFAP is an early marker of stellate cell activation. GFAP mRNA levels were significantly higher in livers from vehicle-treated controls compared with vehicle-treated ethanol-exposed rats. GFAP expression was significantly increased by PPAR-α treatment in both control and ethanol-exposed rats (FIG. 11D), and in the ethanol-fed group, PPAR-γ treatment significantly increased GFAP expression relative to vehicle-treatment.

Desmin is an intermediate filament expressed in stellate cells during transdifferentiation into myofibroblast-like cells. The mean levels of desmin mRNA were similar in vehicle-treated control and ethanol-exposed livers (FIG. 11E). However, in the control group, treatment with the PPAR-δ or PPAR-γ agonist significantly reduced desmin mRNA levels relative to vehicle. In ethanol-exposed livers, treatment with the PPAR-γ agonist significantly increased desmin mRNA expression relative to vehicle treatment, whereas treatment with the PPAR-α or PPAR-δ agonist had no significant effect on desmin mRNA levels.

Collagen gene expression reflects fibrogenesis. Collagen mRNA expression was lowest in vehicle-treated control livers (FIG. 11F). Although the PPAR agonist treatments increased the mean levels of collagen gene expression in controls, the differences relative to vehicle were statistically significant only for the PPAR-δ treated group. Chronic ethanol exposure significantly increased the mean levels of collagen mRNA relative to control (vehicle-treated subgroups). In rats fed with ethanol-containing diets, treatment with the PPAR-α agonist further increased collagen gene expression, whereas the PPAR-δ and PPAR-γ agonists significantly reduced the mean level of collagen mRNA relative to vehicle treatment.

Figure 12:
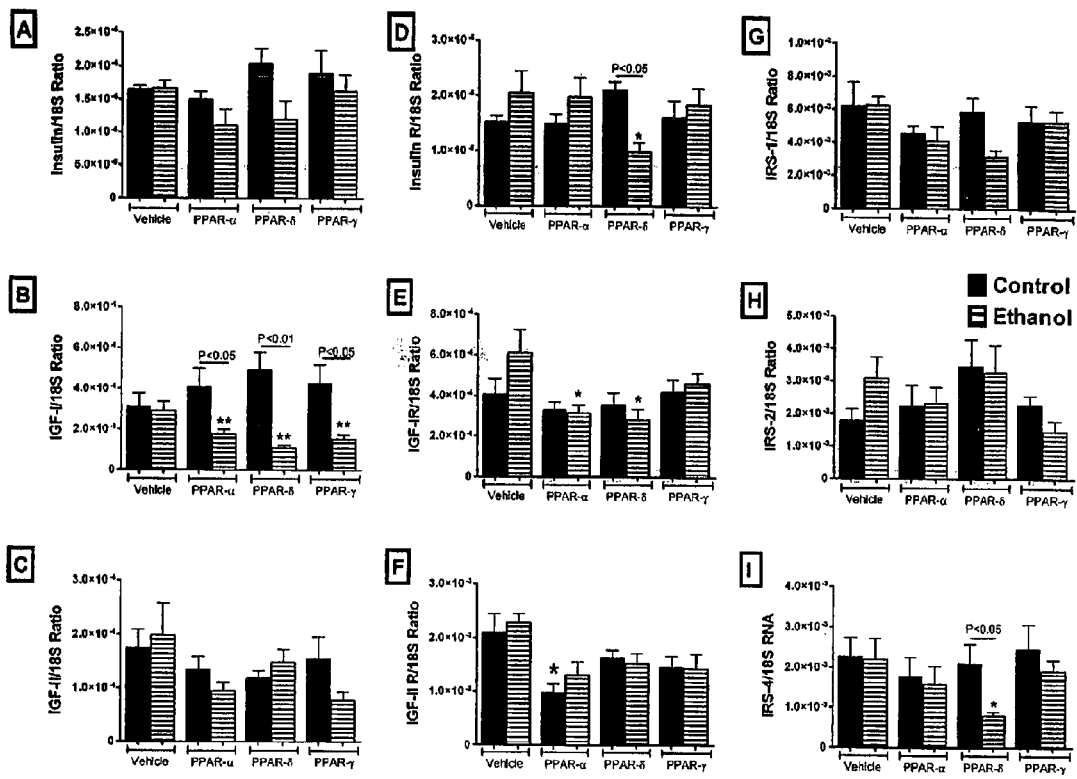
FIGS. 12A-12I show the effects of ethanol and PPAR agonists on hepatic expression of insulin and IGF polypeptides, their receptors, and IRS molecules.

Effects of Ethanol and PPAR Agonists on Hepatic Expression of Insulin and IGF Polypeptides, their Receptors, and IRS Molecules:

QRT-PCR studies demonstrated expression of insulin, IGF-I, IGF-II polypeptide genes, their corresponding receptors, and IRS-1, IRS-2, and IRS-4 in livers of both control and ethanol-fed rats (FIG. 12), indicating that the upstream genes required for insulin and IGF signaling are all expressed in adult rat livers. Among the polypeptide genes, insulin was least abundant, followed by IGF-II, and IGF-I was most abundant (FIGS. 12A-12C). Vehicle-treated control and ethanol-exposed liver had similar mean mRNA levels of insulin, IGF-I and IGF-II. In the control group, PPAR-δ and PPAR-γ significantly increased insulin gene expression, whereas in the ethanol-exposed group, insulin gene expression was reduced by PPAR-α or PPAR-δ treatment. Insulin gene expression was significantly lower in ethanol-exposed PPAR-δ and PPAR-γ treated relative to corresponding control livers. IGF-I mRNA levels were not significantly modulated by PPAR agonist treatments in control rats, but in the ethanol-exposed group, PPAR agonist treatments significantly reduced IGF-I expression relative to vehicle and all corresponding PPAR agonist-treated controls (FIG. 12B). In controls, IGF-II expression was also not significantly modulated by PPAR agonist treatment, but with chronic ethanol feeding, PPAR-δ or PPAR-γ treatment significantly reduced the mean levels of IGF-II mRNA relative to vehicle and all corresponding PPAR agonist treated controls (FIG. 12C).

IGF-II receptor mRNA transcripts were most abundant (FIG. 12F), followed by IGF-I receptor (FIG. 12E), and then insulin receptor (FIG. 12D). In controls, treatment with the PPAR-δ agonist increased the mean levels of insulin receptor expression relative to vehicle. Chronic ethanol feeding significantly increased the mean levels of insulin receptor expression relative to control, but in contrast to its effect in controls, the PPAR-δ agonist significantly reduced insulin receptor expression in ethanol-fed rat livers (FIG. 12D). In controls, IGF-I receptor expression was similarly abundant irrespective of PPAR agonist treatment. Chronic ethanol feeding significantly increased the mean levels of IGF-I receptor expression, but the PPAR agonist treatments reduced IGF-I receptor mRNA levels to those observed in corresponding controls (FIG. 12E). IGF-II receptor expression was similarly abundant in control and ethanol-exposed livers, and PPAR agonist treatments similarly reduced the mean levels of IGF-II receptor mRNA in both groups (FIG. 12F).

In both control and ethanol-exposed livers, IRS-1 mRNA levels were highest (FIG. 12G), followed by IRS-2 (FIG. 12H), and then IRS-4 (FIG. 12I). The mean levels of IRS-1 were similar for control and ethanol-fed rats (FIG. 12G). The PPAR agonist treatments did not significantly alter IRS-1 gene expression in controls, but in ethanol-fed rats, PPAR-δ treatment significantly reduced IRS-1 mRNA levels relative to vehicle and the corresponding PPAR-δ treated controls. The mean level of IRS-2 expression was significantly higher in ethanol-exposed relative to control livers (FIG. 12H). In the control group, IRS-2 expression was significantly increased by treatment with the PPAR-δ agonist, whereas in ethanol-exposed rats, IRS-2 expression was significantly reduced by treatment with the PPAR-γ agonist. The mean levels of IRS-4 mRNA were similar for control and ethanol-exposed livers, and in the control group, treatment with PPAR agonists did not significantly alter the mean levels of IRS-4 expression (FIG. 12I). In contrast, in the ethanol-exposed group, treatment with the PPAR-δ agonist significantly reduced the mean level of IRS-4 expression, similar to its effect on IRS-1 (see above).

Figure 13:
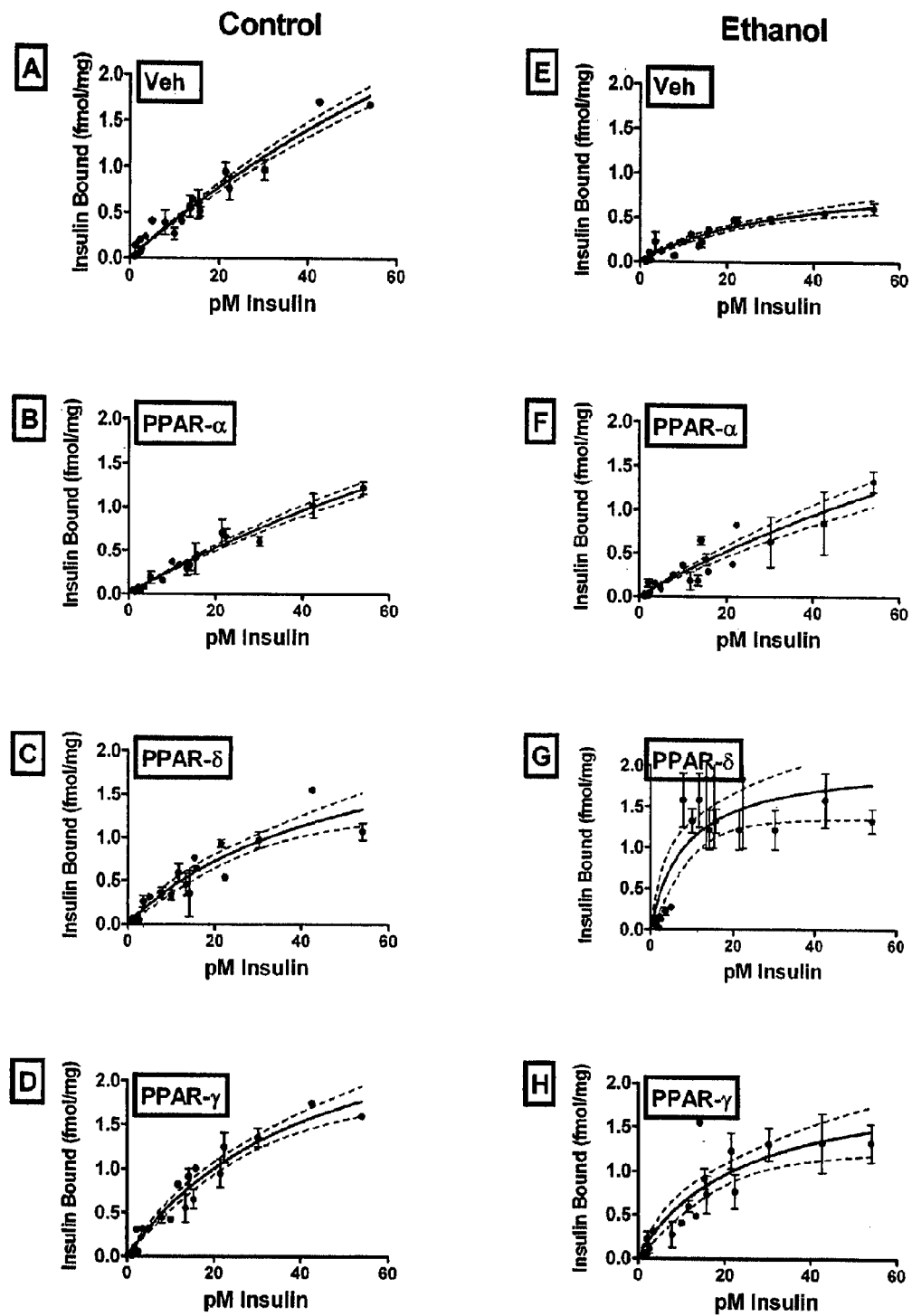
FIGS. 13A-13H show the effects of ethanol and PPAR agonist treatments on insulin receptor binding.

Effects of Ethanol and PPAR Agonist Treatments on Insulin and IGF Receptor Binding:

Saturation binding assays were used to demonstrate the effects of ethanol and PPAR agonist treatments on insulin, IGF-I and IGF-II receptor binding. The studies were performed with pooled liver tissue samples from 8 rats (equal proportions by protein content) within each subgroup. Binding curves±95% C.I.L., computations of Kd (dissociation constant; affinity) and BMAX (top-level binding), and inter-group statistical comparisons were generated with Prism Graphics 5 software. In all experimental conditions, a single-site model produced the highest $R^2$, i.e., best fit. Chronic ethanol feeding significantly reduced the BMAX, but had no significant effect on the Kd for insulin receptor binding (FIGS. 13A, 13E and Table 3). In the control group, the BMAX for insulin receptor binding was significantly reduced by treatment with a PPAR-α, PPAR-δ, or PPAR-γ agonist (FIGS. 13A-13D and Table 3). The PPAR-α treatment had the most pronounced effect in terms of reducing the insulin receptor BMAX. In contrast, PPAR agonist treatments did not significantly alter the Kd for insulin binding. In ethanol-exposed rats, PPAR-α treatment also blunted the BMAX and increased the Kd relative to vehicle, whereas treatment with a PPAR-δ or PPAR-γ agonist significantly increased insulin receptor BMAX and lowered the Kd, indicating higher levels of maximum binding and increased binding affinity relative to both vehicle and corresponding PPAR agonist treated control livers (FIGS. 13E-13H and Table 3).

TABLE 3

| Group | BMAX ± S.E.M. | 95% C.I.- BMAX | KD ± S.E.M | 95% C.I.- KD | $R^2$ |
|---|---|---|---|---|---|
| Insulin receptor binding | | | | | |
| Control + Vehicle | 7.23 ± 2.66 | 1.83-12.63 | 165.5 ± 73 | 16.6-314.5 | 0.929 |
| Control + PPAR-α | 1.03 ± 0.16*** | 0.69-1.36 | 34.0 ± 9.4*** | 14.93-53.14 | 0.884 |
| Control + PPAR-δ | 4.93 ± 1.99 | 0.89-8.97 | 165.7 ± 80.7 | 2.23-329.1 | 0.920 |
| Control + PPAR-γ | 8.06 ± 10.73 | −13.78-29.91 | 300.6 ± 448.5 | −612.4-1214 | 0.778 |
| Ethanol + Vehicle | 2.59 ± 0.61** | 1.36-3.82 | 51.38 ± 18.63*** | 13.62-89.15 | 0.84 |
| Ethanol + PPAR-α | 2.04 ± 0.35*** | 1.33-2.75 | 8.45 ± 4.06*** | 0.21-16.69 | 0.57 |

TABLE 3-continued

| Group | BMAX ± S.E.M. | 95% C.I.-BMAX | KD ± S.E.M | 95% C.I.-KD | $R^2$ |
|---|---|---|---|---|---|
| Ethanol + PPAR-δ | 3.21 ± 0.45** | 2.29-4.12 | 43.85 ± 9.91** | 23.76-63.94 | 0.92 |
| Ethanol + PPAR-γ | 2.08 ± 0.42*** | 1.22-2.93 | 23.26 ± 9.33** | 4.3-42.22 | 0.746 |
| IGF-I receptor binding | | | | | |
| Control + Vehicle | 3.62 ± 0.77 | 2.04-5.21 | 131.9 ± 49.7 | 30.64-233.1 | 0.79 |
| Control + PPAR-α | 2.52 ± 0.31** | 1.87-3.16 | 63.3 ± 16.2** | 30.2-95.4 | 0.84 |
| Control + PPAR-δ | 1.64 ± 0.37** | 0.88-2.39 | 57.2 ± 27.1 | 0.88-2.4 | 0.48 |
| Control + PPAR-γ | 6.43 ± 2.00* | 2.32-10.63 | 425.7 ± 178.1** | 80.9-790.4 | 0.91 |
| Ethanol + Vehicle | 2.66 ± 0.38* | 1.88-3.45 | 43.57 ± 13.71** | 15.49-71.68 | 0.78 |
| Ethanol + PPAR-α | 4.21 ± 0.88 | 2.42-6.00 | 127.3 ± 45.86 | 32.2-222.4 | 0.76 |
| Ethanol + PPAR-δ | 3.81 ± 0.89 | 1.99-5.62 | 120.6 ± 52.1 | 14.4-226.8 | 0.71 |
| Ethanol + PPAR-γ | 2.74 ± 0.91 | 0.87-4.60 | 100.1 ± 63.2 | −28.9-229.0 | 0.48 |
| IGF-II receptor binding | | | | | |
| Control + Vehicle | 40.12 ± 3.04 | 33.96-46.27 | 29.3 ± 5.8 | 17.6-40.9 | 0.92 |
| Control + PPAR-α | 40.27 ± 3.28 | 33.62-46.9 | 31.4 ± 6.4 | 18.3-44.5 | 0.91 |
| Control + PPAR-δ | 29.01 ± 1.99*** | 24.99-33.04 | 21.5 ± 4.3 | 12.6-29.9 | 0.91 |
| Control + PPAR-γ | 25.20 ± 2.04*** | 21.06-29.34 | 14.6 ± 3.9** | 6.6-22.6 | 0.83 |
| Ethanol + Vehicle | 22.63 ± 5.25* | 12.00-33.25 | 32.4 ± 18.7 | −5.5-70.4 | 0.53 |
| Ethanol + PPAR-α | 28.88 ± 6.20 | 16.31-41.44 | 40.5 ± 20.0 | 16.3-41.4 | 0.59 |
| Ethanol + PPAR-δ | 51.50 ± 13.53 | 24.11-78.90 | 75.6 ± 37.1 | 0.52-150.8 | 0.60 |
| Ethanol + PPAR-γ | 22.56 ± 4.43* | 13.60-31.53 | 32.3 ± 15.8 | 0.26-64.38 | 0.60 |

*$P < 0.05$;
**$P < 0.001$;
***$P < 0.0001$ relative to Control + Vehicle

Figure 14:
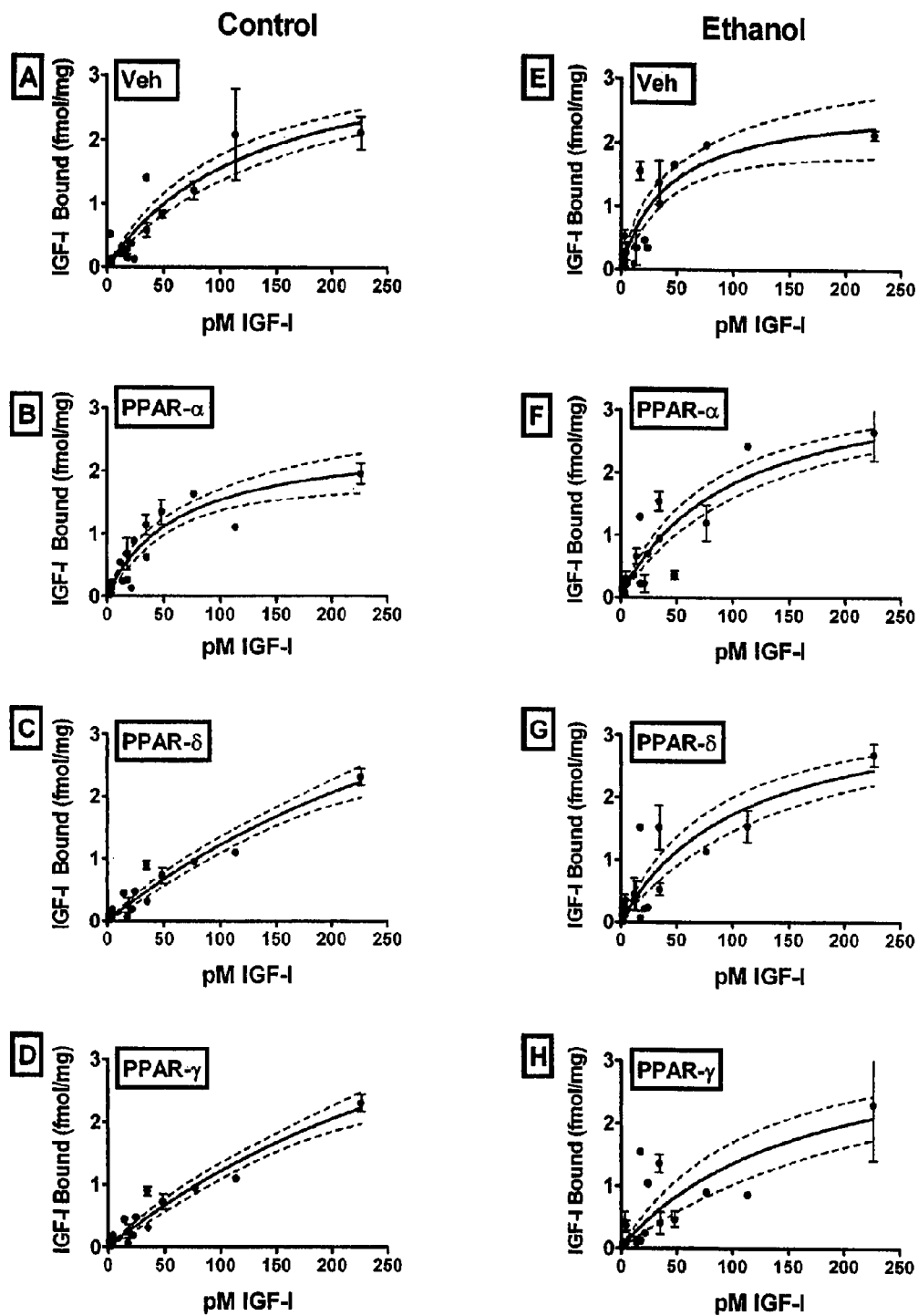
FIG. 14A-14H show the effects of ethanol and PPAR agonist treatments on IGF-I receptor binding.
Figure 15:
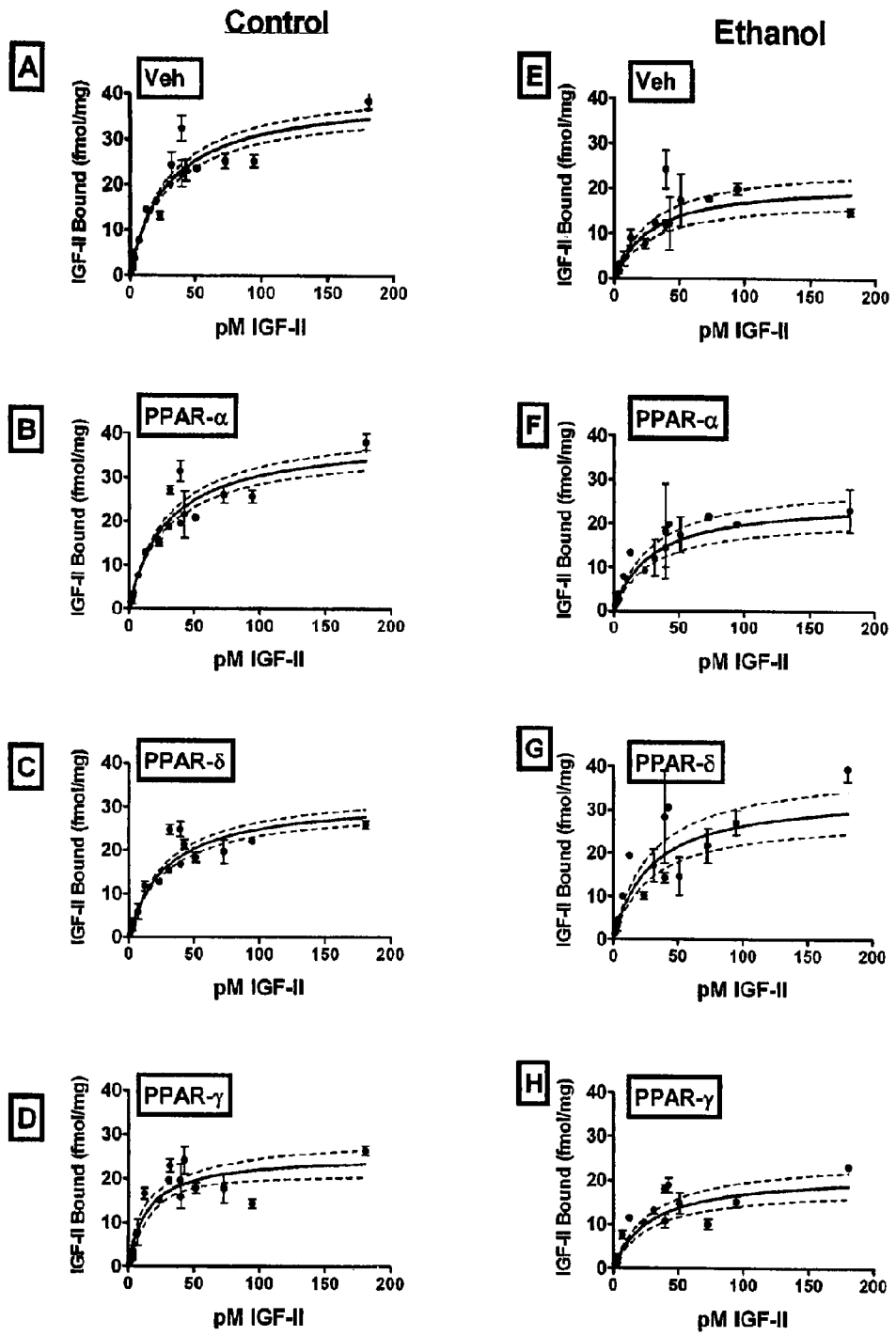
FIG. 15A-15H show the effects of ethanol and PPAR agonist treatments on IGF-II receptor binding.

Chronic ethanol feeding significantly reduced IGF-I BMAX and Kd. In control-fed rats, PPAR-α treatment reduced the IGF-I BMAX, while PPAR-δ and PPAR-γ treatments significantly increased the IGF-I BMAX (FIG. 14). PPAR agonist treatments did not significantly alter the IGF-I Kd in control fed rats (FIGS. 14A-14D). In the ethanol-fed rats, PPAR-α or PPAR-δ treatment significantly increased both the BMAX and Kd, whereas PPAR-γ treatment increased the Kd, but lowered the BMAX for IGF-I receptor binding (FIGS. 14E-14H). Chronic ethanol feeding also significantly reduced the BMAX and increased the Kd of IGF-II receptor binding, and PPAR agonist treatments had no significant effect on the BMAX or the Kd in either the control or ethanol-exposed groups (FIG. 15 and Table 3).

Effects of Ethanol and PPAR Agonist Treatments on Insulin/IGF Responsive Gene Expression Related to Energy Metabolism and Tissue Remodeling:

AAH expression increases with insulin, IGF-I, or IGF-II stimulation and has positive effects on hepatocellular growth and motility (Cantarini et al., Hepatology 44:446 (2006); de la Monte et al., J. Hepatol. 44:971 (2006)). GAPDH is an insulin-responsive gene that has an important role in glucose metabolism. Western blot analysis detected AAH and GAPDH immunoreactivities in all liver samples (FIG. 16A). Re-probing of the blots with monoclonal antibody to β-actin demonstrated approximately equal protein loading in all lanes. Digital image quantification of the Western blot signals revealed lower levels of AAH and GAPDH in ethanol-exposed vehicle-treated livers. In controls, PPAR agonist treatments had no detectable effect on the mean levels of AAH (FIG. 16B), but slightly (although not significantly) modulated the mean levels of GAPDH (FIG. 16C) and β-actin (FIG. 16D). PPAR agonist treatments also slightly but not significantly modulated hepatic AAH and GAPDH expression in ethanol-fed group. The net shifts in mean levels of AAH and GAPDH protein abolished the significant inter-group differences in AAH and/or GAPDH protein expression. However, to examine the effects of PPAR agonist treatment with greater refinement, a highly sensitive direct ELISA assay with fluorescent reporter reagents was used.

Figure 17:
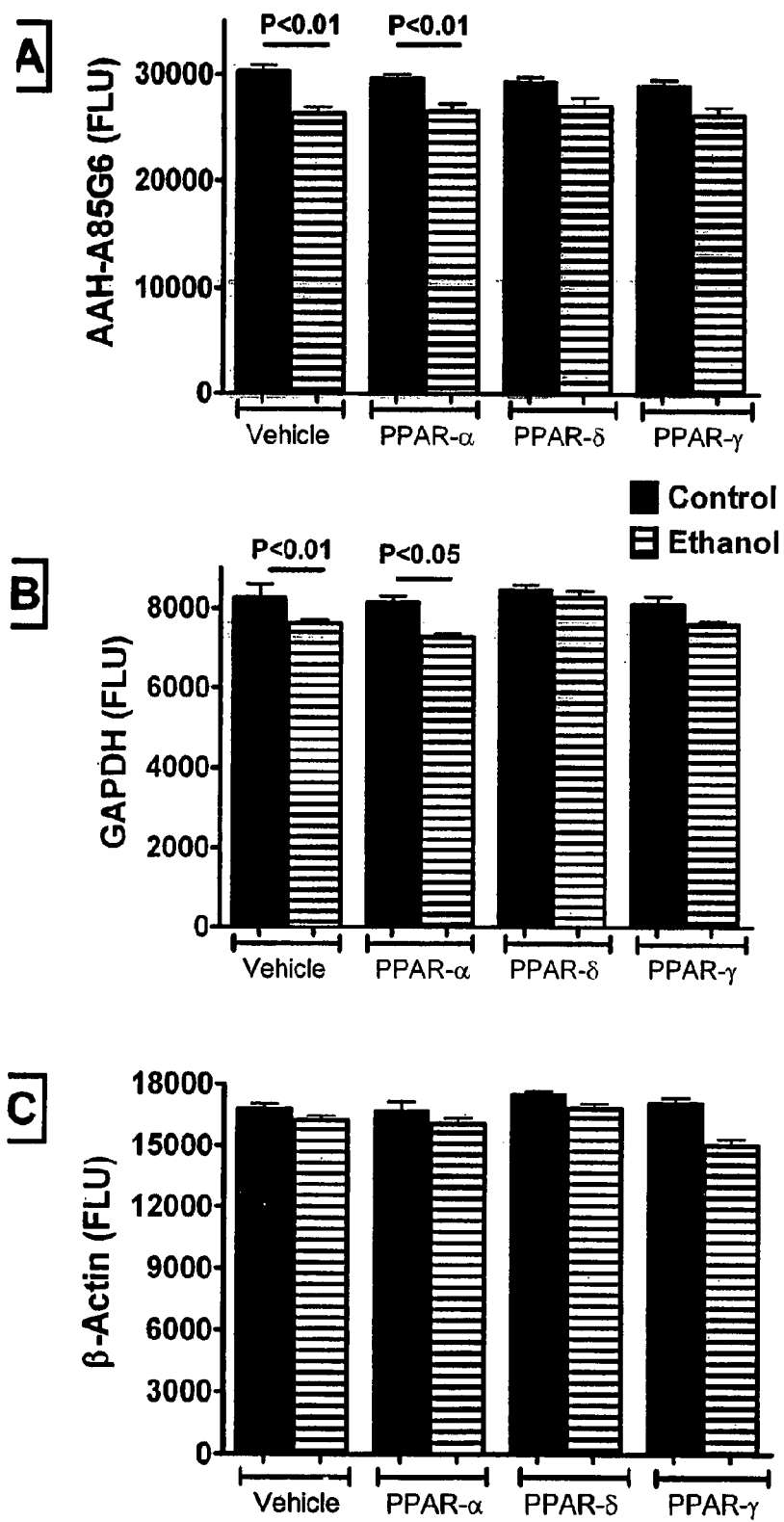
FIG. 17A-17C show the effects of ethanol and PPAR agonist treatments on AAH and GAPDH expression by ELISA analysis.

ELISAs also demonstrated significantly lower mean levels of AAH (FIG. 17A) and GAPDH (FIG. 17B) expression in ethanol exposed relative to control livers (vehicle-treated). Treatment with the PPAR-α agonist had no significant effect on either AAH or GAPDH expression in either control or ethanol-exposed livers. In contrast, treatment with the PPAR-δ or PPAR-γ agonist increased GAPDH expression in ethanol-exposed livers, resulting in mean levels that were comparable to control. Treatment with PPAR-δ or PPAR-γ agonist slightly reduced AAH expression in control livers, resulting in AAH levels that were similar to those in the corresponding ethanol-fed groups. β-actin immunoreactivity was not significantly modulated by ethanol exposure or PPAR agonist treatment, and therefore no significant inter-group differences in the mean levels of β-actin were observed (FIG. 17C).

This study was designed to determine if chronic ALD produced in the Long Evans rat model was associated with hepatic insulin resistance, and at the same time, explored the hypothesis that insulin sensitizer agents could be used to restore liver histology in the clinical setting of continued ethanol consumption. To conduct these studies, rats were treated with a PPAR-α, PPAR-δ, or PPAR-γ agonist. This approach was taken because exploratory studies demonstrated that all three receptors are expressed in liver yet there was no definitive data indicating which class of PPAR agonist would be most suitable for restoring hepatic structure and function in ALD.

The chronic ethanol feeding produced histopathological changes that resemble ALD in humans, including prominent architectural disarray with variation in nuclear size and hepatocyte drop-out, yet there was no evidence of interlobular or bridging fibrosis, cirrhosis, regenerative nodule formation, or neoplastic transformation. Treatment with a PPAR-α, PPAR-δ, or PPAR-γ agonist produced no detectable effects on liver histology in controls, but they strikingly reduced the ethanol-associated architectural disarray and steatosis, despite continued ethanol exposure. The PPAR-δ and PPAR-γ agonists were more effective than the PPAR-α agonist in restoring hepatic architecture. These effects of the PPAR agonists correspond with their known anti-inflammatory actions, in addition to their insulin sensitizer properties.

To more objectively quantify the effects of the PPAR agonist treatments on liver histology, a method of evaluating relative expression of specific genes corresponding to different cell types, i.e., liver cell profiling, was used. These analyses demonstrated that chronic ethanol exposure significantly reduced albumin and ASBT expression, suggesting that chronic ethanol feeding significantly reduced hepatocyte and bile duct epithelial cell abundance and/or function. Overall, the PPAR agonist treatments increased albumin and ASBT expression in both control and ethanol-exposed livers; however the effects differed with respect to which subtype of PPAR agonist was most effective and the magnitude of the responses. In this regard, PPAR-α and PPAR-δ agonists normalized albumin and ASBT expression in ethanol-exposed livers, whereas PPAR-δ and PPAR-γ agonists significantly increased albumin and decreased ASBT expression in control livers. These findings suggest that PPAR agonist treatments may have beneficial effects on hepatocyte and biliary epithelial cell survival and function. The increased expression of KCR observed in ethanol-exposed, PPAR agonist treated livers is of uncertain significance. One possible interpretation is that, in correlation with the improvements in liver histology, increased Kuppfer cell function is needed to manage the repair process.

GFAP and desmin are markers of stellate cell activation and proneness toward a fibrogenic response. Collagen gene expression was used as an index of active fibrogenesis. The results demonstrated that expression levels of both GFAP and collagen were increased by PPAR-α treatment in control and ethanol-fed rats, suggesting that PPAR-α agonists may activate stellate cells and ultimately promote fibrogenesis, an effect that may be worse in the setting of ALD. In contrast, treatment with the PPAR-δ agonist reduced collagen gene expression in ethanol-fed rats, but increased it in control rats, and PPAR-γ agonist treatment only increased desmin expression in ethanol-exposed livers. Although these results are complex, one potential interpretation is that certain degrees of stellate cell and fibrogenic response may be required for liver repair in the context of chronic ethanol-induced liver injury.

QRT-PCR analysis was used to assess the integrity of "machinery" required for insulin and IGF signaling. The studies demonstrated that the expression levels of the insulin, IGF-I and IGF-II polypeptides, the corresponding receptors, and IRS molecules were relatively preserved in chronic ethanol-exposed livers, indicating that impairments in insulin or IGF signaling caused by chronic ethanol exposure could not be attributed to local growth factor deficiencies, down-regulation or loss of receptors, or impaired expression of major docking molecules that transmit downstream signals. Of note was that treatment with the PPAR-δ or PPAR-γ agonist significantly increased insulin and IGF-I expression in control livers, but either inhibited or had no significant effect on trophic factor gene expression in ethanol-exposed livers. Similarly, insulin, IGF-I, and IGF-II receptors, and IRS-1, IRS-2, and IRS-4 expression levels were not modulated by PPAR agonist treatments. Therefore, any improvements in liver histology associated with PPAR agonist treatment in ethanol-fed rats were not due to increased expression of local growth factors, growth factor receptors, or IRS genes.

Effective ligand binding is critical to the signaling cascade, and many of the downstream effects of impaired insulin signaling that have been reported in ethanol-exposed livers, including reduced cell survival, could be mediated by inhibition of insulin binding to its receptor. Given the fact that signaling through IGF-I or IGF-II activates IRS pathways either directly or via cross-talk, it was of interest to also measure IGF-I and IGF-II receptor binding in these models. The studies using competitive saturation binding assays demonstrated that chronic ethanol exposure significantly impairs ligand binding to the insulin, IGF-I, and IGF-II receptors as manifested by the reduced BMAX (top-level binding) and increased Kd (reduced affinity). The PPAR-δ, and in some instances PPAR-γ agonist treatments significantly increased insulin, IGF-I, and/or IGF-II receptor binding resulting in higher, i.e., normalized BMAX values in ethanol-exposed livers. Although the mechanism of increased receptor binding has not yet been determined, this effect could have been mediated by corrections in membrane lipid composition since in previous studies, it has been demonstrated that ligand binding to the insulin and IGF receptors was impaired due to membrane cholesterol depletion, and restored by membrane cholesterol repletion. Regardless of mechanism, it is likely that the PPAR agonist associated increases in insulin and IGF receptor binding had critical roles in restoring liver structure and function, including insulin/IGF responsive gene expression, despite continued ethanol exposure.

To examine the consequences of PPAR agonist-mediated increases in insulin and IGF receptor binding in ethanol-exposed livers, insulin and IGF responsive gene expression was assessed by Western blot analysis and ELISA. As expected, the ethanol-exposed livers of vehicle-treated rats had significantly reduced levels of GAPDH and AAH, which respectively mediate energy metabolism and cell motility required for regeneration and remodeling of tissue Treatment with a PPAR-δ or PPAR-γ agonist significantly increased GAPDH expression, resulting in normalization of levels relative to vehicle-treated controls. Therefore, the downstream consequences of increased ligand-receptor binding were increased insulin/IGF responsive gene expression and/or improved liver histology, despite continued ethanol exposure. Importantly, increased levels of GAPDH may be an important factor in the reduction of steatosis due to improved energy metabolism and ATP production, whereas increased AAH expression could have aided in liver remodeling and repair, thereby helping to maintain relatively normal liver histology. Together, the results suggest that PPAR agonist treatments may be helpful for reversing some of the adverse effects of chronic ALD, particularly with respect to the restoration of liver structure and function.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

What is claimed is:

1. A method for decreasing insulin resistance in the liver of a human diagnosed with alcohol-induced liver disease or alcohol induced liver damage comprising administering to said human at least one peroxisome proliferator activated receptor-δ (PPAR-δ) selective agonist in a therapeutically effective amount, wherein said PPAR-δ agonist is selected from the group consisting of GW-501516, GW-0742, L-165041, carbaprostacyclin, and RWJ-800025.

2. The method of claim 1, wherein said liver damage is produced by chronic alcohol intake in said human.

3. The method of claim 1, wherein two or more PPAR agonists are administered.

4. The method of claim 1, wherein, said liver disease is steatosis, alcoholic hepatitis, or alcoholic cirrhosis.

5. The method of claim 2, wherein said chronic alcohol intake is at least about 0.1 g pure alcohol/kg body weight/day on average.

6. The method of claim 2, wherein said chronic alcohol intake is at least about 0.5 g pure alcohol/kg body weight/day on average.

7. The method of claim 2, wherein said chronic alcohol intake is at least about 1 g pure alcohol/kg body weight/day on average.

8. The method of claim 1, wherein said PPAR-δ selective agonist comprises L-165,041.

9. The method of claim 2, wherein alcohol intake constitutes at least 37% by caloric content for at least 6 weeks.

10. The method of claim 1, wherein said insulin resistance is determined by measuring insulin binding to the insulin receptor, glucose tolerance tests, or expression of insulin-responsive genes.

* * * * *